United States Patent
Williams et al.

(10) Patent No.: US 10,898,690 B2
(45) Date of Patent: Jan. 26, 2021

(54) VASCULAR ACCESS DISASSEMBLING NEEDLE DEVICE AND METHOD

(71) Applicant: Government of the United States as Represented by the Secretary of the Air Force, Wright-Patterson AFB, OH (US)

(72) Inventors: Timothy K Williams, Winston-Salem, NC (US); Lucas Paul Neff, Winston-Salem, NC (US); James B Sampson, Davis, CA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 56 days.

(21) Appl. No.: 16/087,214

(22) PCT Filed: Mar. 20, 2017

(86) PCT No.: PCT/US2017/023215
§ 371 (c)(1),
(2) Date: Sep. 21, 2018

(87) PCT Pub. No.: WO2017/165298
PCT Pub. Date: Sep. 28, 2017

(65) Prior Publication Data
US 2019/0099587 A1    Apr. 4, 2019

Related U.S. Application Data

(60) Provisional application No. 62/311,447, filed on Mar. 22, 2016.

(51) Int. Cl.
*A61M 25/06*    (2006.01)
*A61M 25/01*    (2006.01)
(Continued)

(52) U.S. Cl.
CPC .......... *A61M 25/065* (2013.01); *A61B 17/34* (2013.01); *A61B 17/3403* (2013.01);
(Continued)

(58) Field of Classification Search
CPC .. A61M 25/01; A61M 25/06; A61M 25/0662; A61M 25/0169; A61M 25/065;
(Continued)

(56) References Cited

U.S. PATENT DOCUMENTS

| 3,382,872 A | 5/1968 | Rubin |
| 3,610,239 A | 10/1971 | Huggins |

(Continued)

FOREIGN PATENT DOCUMENTS

| WO | WO-2015148478 A1 * | 10/2015 | ........ A61M 25/0668 |
| WO | 2015148478 | 6/2017 | |

OTHER PUBLICATIONS

United States Patent and Trademark Office, International Search Authority, International Search Report and Written Opinion of the International Searching Authority, dated Jun. 9, 2017, 18 pages total.

*Primary Examiner* — Jason E Flick
(74) *Attorney, Agent, or Firm* — AFMCLO/JAZ; Chastity D. S. Whitaker

(57) ABSTRACT

A vascular access disassembling needle assembly 20 is provided that enables rapid insertion of a guide wire into the needle and subsequent rapid removal of the access needle off the guide wire by facile disassembly of the needle. The disassembling needle assembly 20 includes a needle portion 30 wherein the needle breaks apart by splitting along at least one seam 40 that extends from the proximal to the distal end to allow removal of the guide wire. Various mechanical features are described that can facilitate the separation of the needle body along at least one seam. Once one or more (Continued)

seams are separated, the needle body may be removed from the guide wire without the need to withdraw the needle along the length of the guide wire, which permits preloading of expanders and other medical devices onto the guidewire.

4 Claims, 33 Drawing Sheets

(51) Int. Cl.
*A61M 25/09* (2006.01)
*A61B 17/34* (2006.01)

(52) U.S. Cl.
CPC .... *A61M 25/0169* (2013.01); *A61M 25/0668* (2013.01); *A61M 25/09041* (2013.01)

(58) Field of Classification Search
CPC ........ A61M 25/0668; A61M 25/09041; A61B 17/34; A61B 17/3403
See application file for complete search history.

(56) References Cited

U.S. PATENT DOCUMENTS

| | | | |
|---|---|---|---|
| 3,651,807 A | * | 3/1972 | Huggins ............. A61M 25/065 604/161 |
| 3,685,513 A | | 8/1972 | Bellamy, Jr. |
| 4,147,165 A | | 4/1979 | Tauschinski |
| 4,174,165 A | | 4/1979 | Tauschinski |
| 4,377,165 A | | 3/1983 | Luther et al. |
| 4,449,973 A | | 5/1984 | Luther |
| 4,702,735 A | | 10/1987 | Luther et al. |
| 4,776,846 A | | 10/1988 | Wells |
| 5,221,263 A | * | 6/1993 | Sinko ................ A61M 25/0668 604/161 |
| 5,322,512 A | | 6/1994 | Mohiuddin |
| 5,425,717 A | | 6/1995 | Mohiuddin |
| 5,809,822 A | | 9/1998 | Butty |
| 5,951,518 A | | 9/1999 | Licata et al. |
| 6,080,141 A | | 6/2000 | Castro et al. |
| 8,753,313 B2 | | 6/2014 | Kimmel et al. |
| 9,248,264 B2 | | 2/2016 | Okamura |
| 2004/0064147 A1 | | 4/2004 | Struble |
| 2009/0264719 A1 | | 10/2009 | Markle et al. |

* cited by examiner

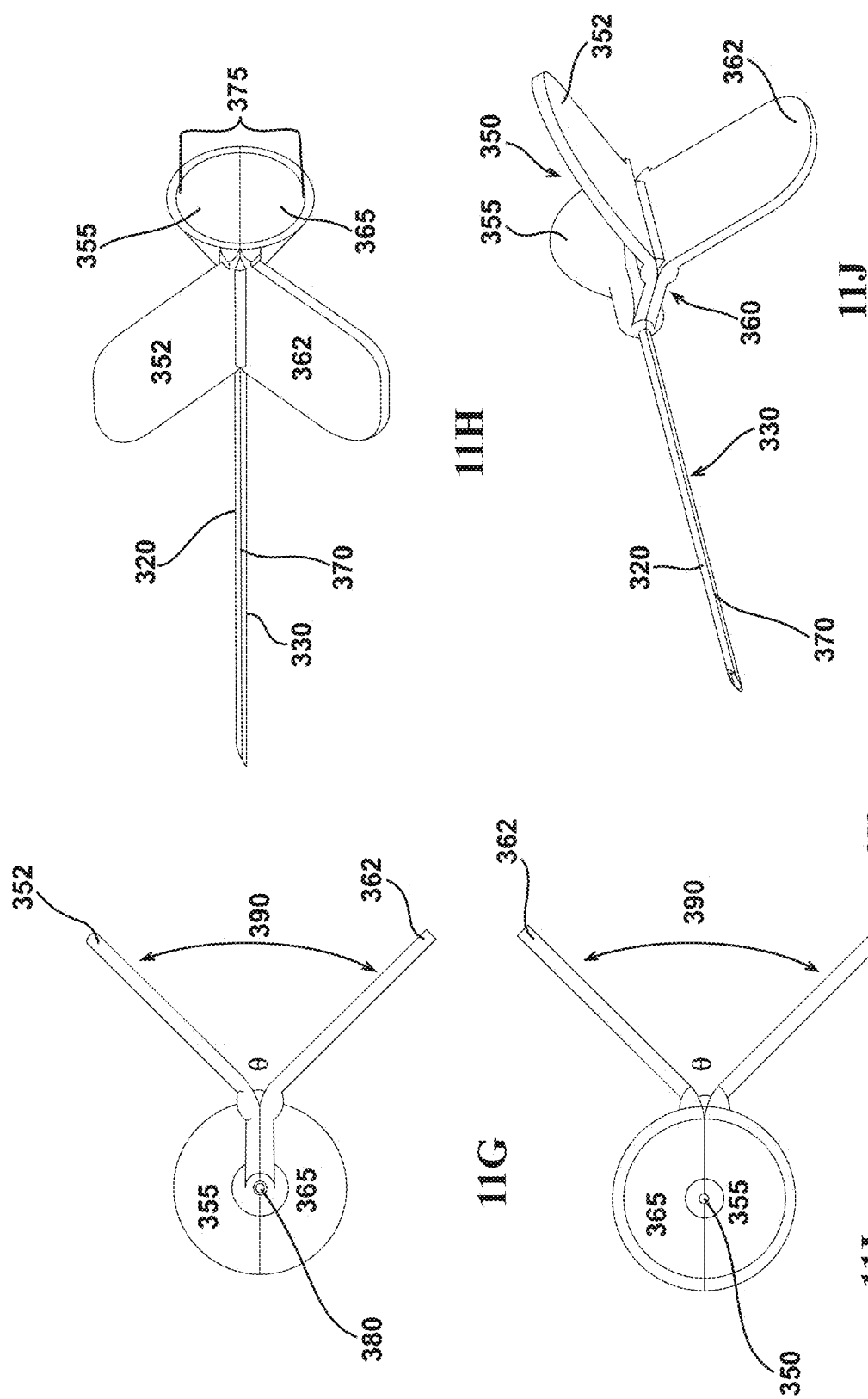

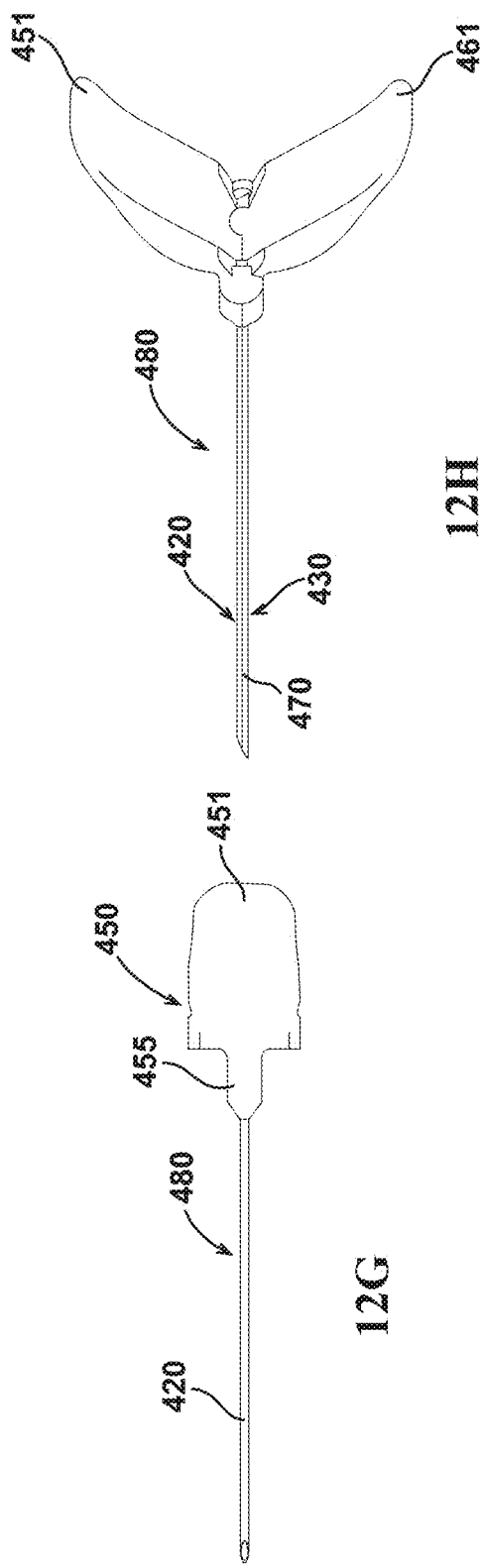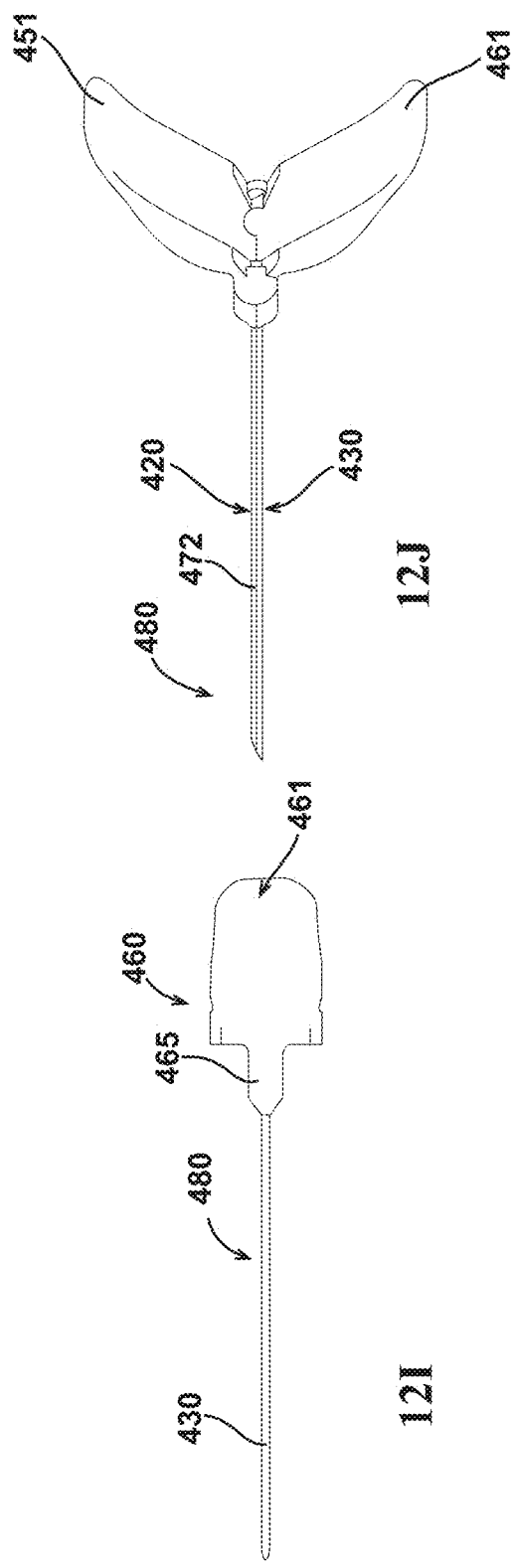
FIGS. 12G-12J

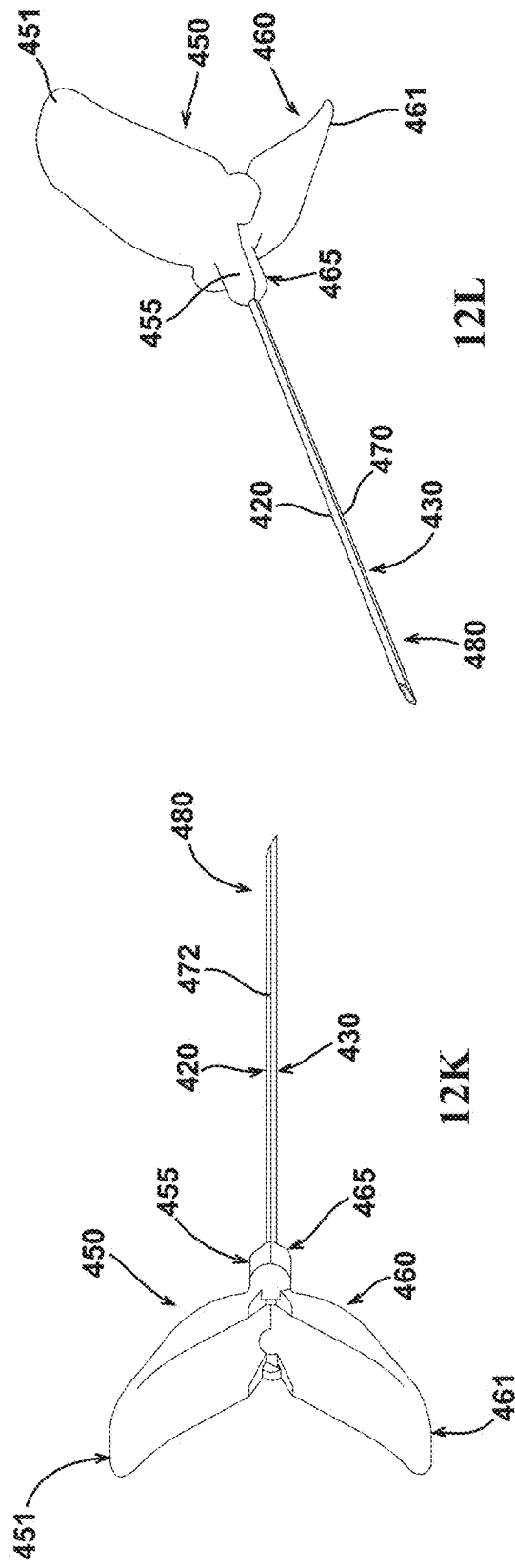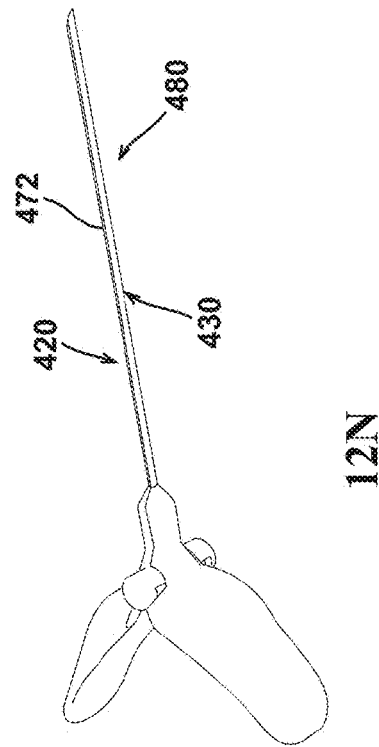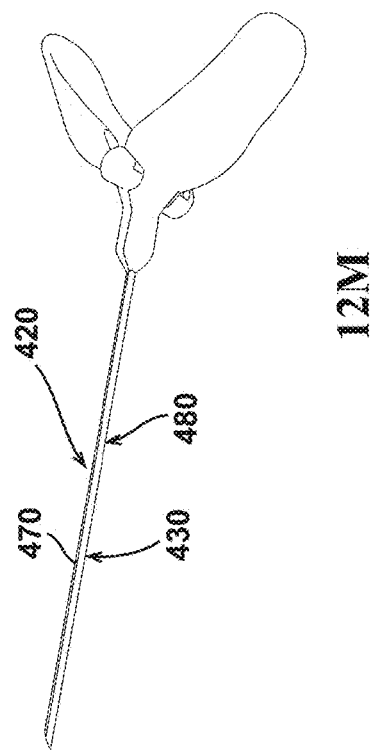
FIGS. 12K-12N

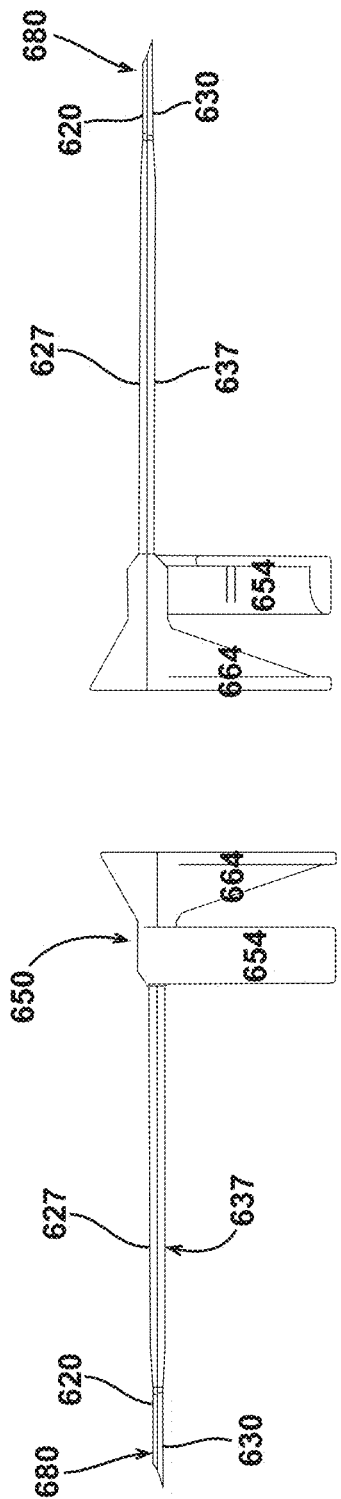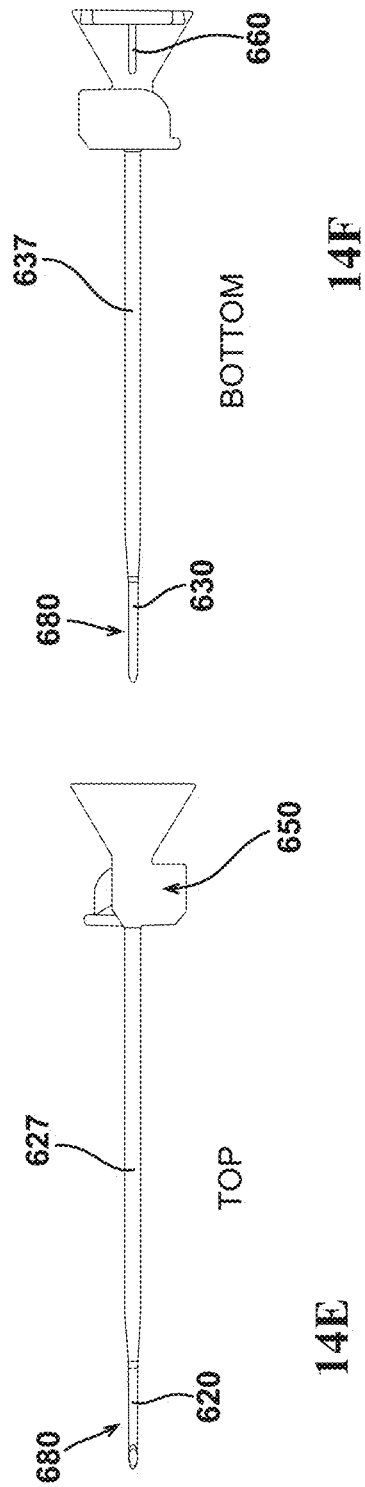
FIGS. 14C-14F

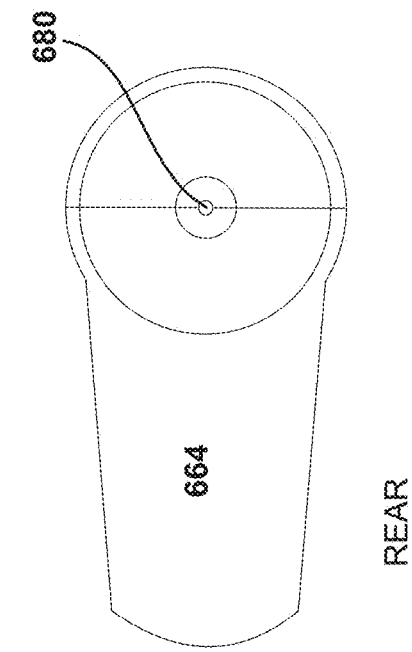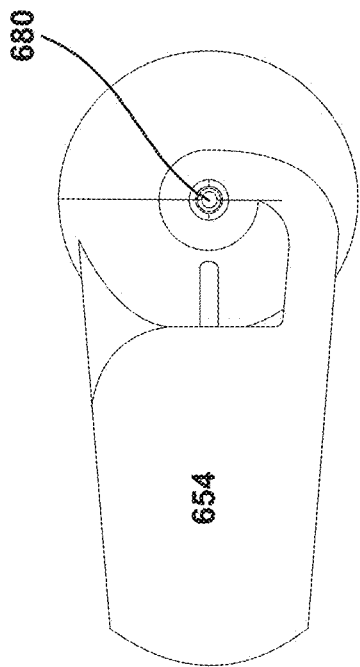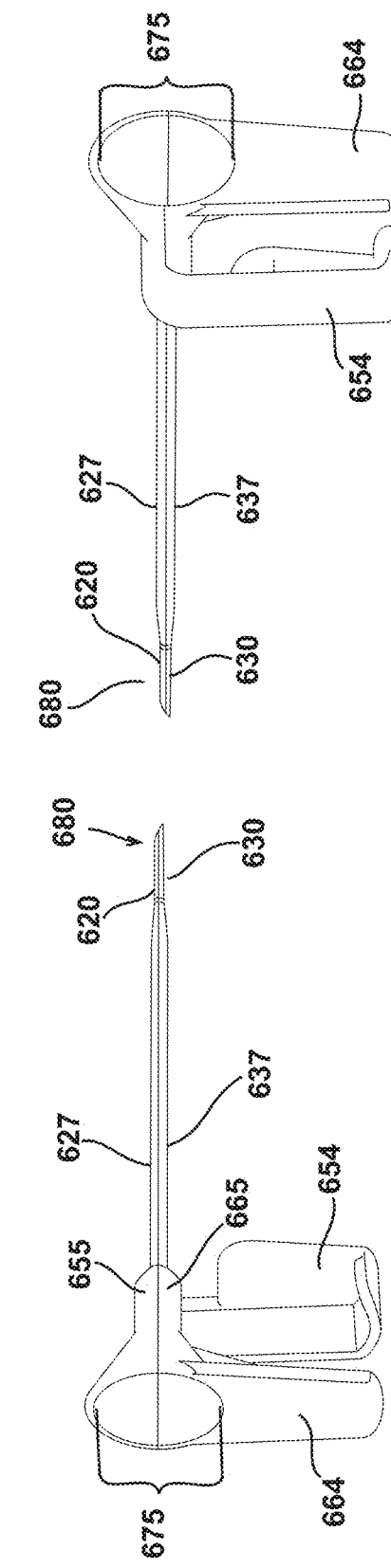
FIGS. 14G-14G

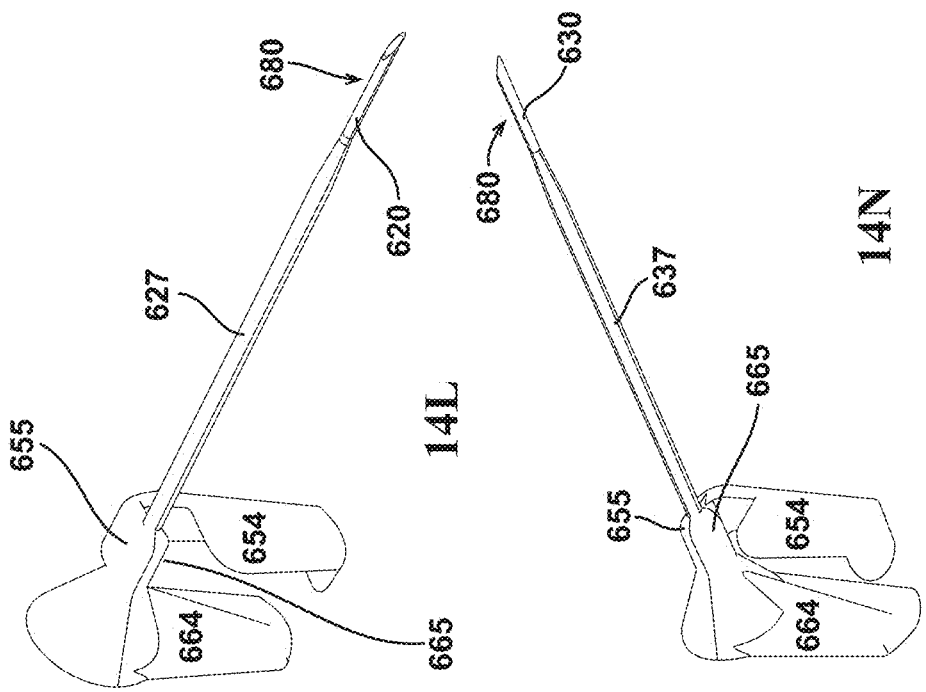
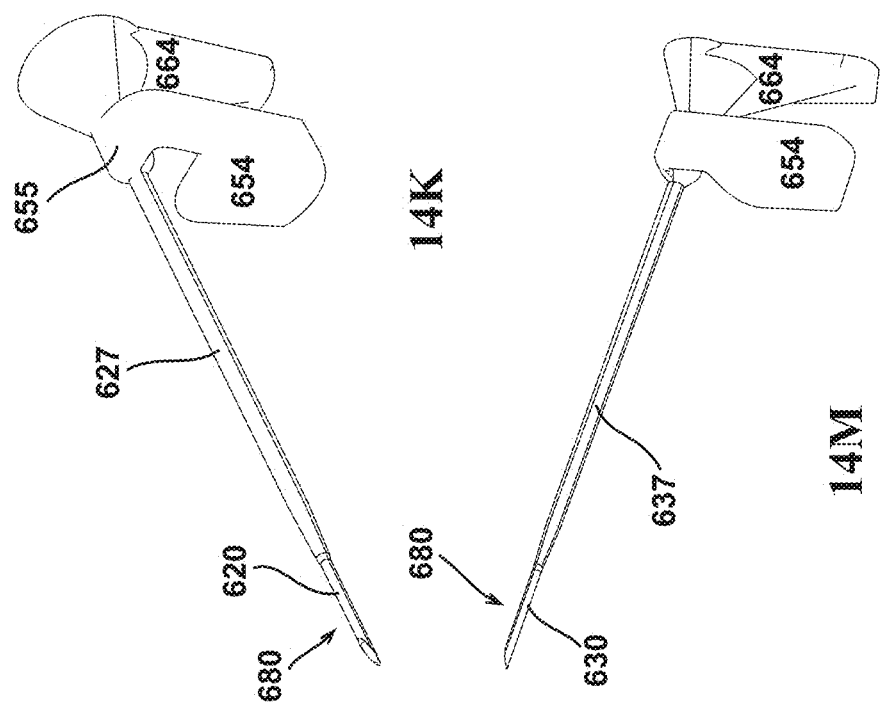
FIGS. 14K-14N

VASCULAR ACCESS DISASSEMBLING NEEDLE DEVICE AND METHOD

CROSS-REFERENCE TO RELATED APPLICATIONS

This application claims priority to U.S. Provisional Patent Application Ser. No. 62/311,447, which was filed on Mar. 22, 2016, and is incorporated by reference into this description in its entirety.

RIGHTS OF THE GOVERNMENT

The invention described herein may be manufactured and used by or for the Government of the United States for all governmental purposes without the payment of any royalty.

FIELD OF THE INVENTION

The present invention is related to medical devices and medical instruments. More particularly, the invention relates to devices and assemblies for facilitating percutaneous insertion of medical devices into a subject.

BACKGROUND OF THE INVENTION

Percutaneous access into various regions of the body is necessary for a wide variety of diagnostic and therapeutic purposes. For example, intravascular catheters are introduced to both the arterial vasculature and the venous vasculature, typically using either direct insertion into a vessel via surgical cut down techniques or via percutaneous introduction techniques through the skin and underlying soft tissues. The most common percutaneous introduction technique is the Seldinger technique.

The Seldinger technique is typically used for angiography, insertion of chest drains and central venous catheters, insertion of percutaneous endoscopic gastrostomy (PEG) tubes using the push technique, insertion of leads for artificial pacemakers or implantable cardioverter-defibrillators, and other interventional medical procedures that involve percutaneous insertion of a device from outside the body into a target body space.

While variations exist, the basic Seldinger technique is illustrated in FIGS. 1 and 2 (both of which are prior art). As shown in FIG. 1 and FIG. 2 (both prior art), the basic Seldinger technique typically consists of six steps. The basic Seldinger technique relies on initially accessing a target location within the body (i.e. a blood vessel or body cavity) with an introducer needle (Step 1). A guide wire is then passed through the introducer needle to maintain the path into the target location (Step 2). The introducer needle is then removed from the guide wire by sliding the introducer needle off the extracorporeal end of the guide wire (Step 3). A separate dilator is then passed over a guide wire to enlarge the diameter of the tissue tract so that it can accommodate a larger introducer sheath or catheter (Step 4). The dilator is removed in the same manner as the original introducer needle by sliding it off the extracorporeal end of the guide wire. With the tract through the tissue maintained with the guide wire and sufficiently enlarged, an introducer sheath or other medical device can then be introduced into the target location by sliding it over the guide wire (Step 5). Finally, the guide wire is withdrawn to allow access through the introducer sheath or via the other medical device (Step 6).

Use of the Seldinger technique requires several steps, most notably, the extracorporeal removal of the introducer needle off the guide wire once guide wire access has been established. Removal of the introducer needle according to the Seldinger technique is accomplished by manually maintaining guide wire position within the intracorporeal target space, withdrawing the needle from the tissues, and then sliding the needle off the extracorporeal end of the guide wire. A longer guide wire can complicate the process of introducer needle removal since the physician or responder must slide the introducer needle off the extracorporeal end of the guide wire. Moreover, additional catheters cannot be threaded along the guide wire for insertion into the body until the introducer needle has been completely withdrawn over and separated from the guide wire. Accordingly, this current method of needle removal along the guidewire increases the time required for catheter insertion, increases the risk of losing control of the guidewire, and prevents the preloading of the subsequent catheters on the guidewire.

In view of the foregoing, there exists a need for new devices and methods for facilitating percutaneous insertion of medical devices into a subject.

SUMMARY

Embodiments of the present invention disclose disassembling needles for facilitating access to vasculature and body cavities for the percutaneous introduction of various instruments and tools. The disassembling needles described herein specifically avoid problems associated with introducer needle removal of standard devices and methods. The disassembling needle includes a sharp tip at the distal end (i.e., farthest from the surgeon) shaped to puncture organic tissue (e.g., epidermal and vascular tissues). The disassembling needle can be used by itself or in conjunction with a standard syringe. A surgeon is able to place the disassembling needle percutaneously into a target location within the body. Once access to a target location is achieved, a surgeon has access to a conical opening at the proximal end (i.e., closest to the surgeon) of the disassembling needle to facilitate guide wire insertion through the disassembling needle and into the target location. Once guide wire access is achieved, the disassembling needle can be completely withdrawn from the target location and slid along the guide wire to allow the tip of the disassembling needle to clear the original epidermal insertion site. The disassembling needle may then be "unbound" and disassembled while still on the guide wire to facilitate rapid needle removal. The disassembling needle may be removed directly off the guide wire; there is no need to slide the disassembling needle off the extracorporeal end of the guide wire.

In accordance with an embodiment of the present invention, a vascular access disassembling needle is provided that comprises a longitudinal cylindrical body, i.e. a needle, having two separable portions. The needle includes two opposing seams (e.g., line of weakness or separated structure), each of which runs the length of the needle. At least one seam separates to create an open channel along the length of the needle. In another embodiment, only one seam separates and the other seam bends to allow the first seam to open up and expose the lumen of the needle.

In accordance with another embodiment, the needle separates along two opposing separation seams, allowing the two portions of the needle to split apart. The portions may include tabs at a proximal end to assist in splitting the needle.

Other embodiments of the disassembling needle according to the invention include alternative configurations adapted to permit at least one seam to separate. One configuration relies on the creation of tensile force on the connectors distributed along the length of the seam to separate the connectors. The tensile force is created by rotational compression of two wings at the proximal end of the needle. A bendable seam opposing a separable seam provides a hinge mechanism about which the wings rotate when pressed together.

In yet another embodiment, a disassembling needle is configured to include at least one of a dual hinged connector, an offset hinged connector, an unassisted sliding configuration, or several variations of an assisted sliding configuration, as further described below.

The procedures for use of the various embodiments of the disassembling needle according to the invention are similar although the specific manner for inducing separation and disassembling of the needle may differ slightly. A distal tip of the needle of the disassembling needle assembly, with or without a detachable syringe, is inserted into a subject's epidermis and into a targeted vascular region. The plunger of the syringe is slightly withdrawn to confirm desired vascular access as indicated by the production of blood in a barrel of said syringe. Next, the syringe is removed from the funnel shaped proximal end of the disassembling needle. The surgeon is then able to insert a guide wire into the funnel shaped proximal end and through a needle shaft of the disassembling needle to pass into the targeted vascular region. The surgeon may then withdraw the disassembling needle from the insertion side outside the epidermis while maintaining position of the guide wire.

The surgeon may then actuate the disassembling of the needle according to one of the embodiments described herein or their equivalents. In one embodiment, the surgeon grasps and compresses together two wings of the disassembling needle to split the needle and the proximal conical collar along one seam to create an open channel along an entire length of the disassembling needle. The needle may then be directly removed from the guide wire without having to slide it off the extracorporeal end of the guide wire.

In yet another embodiment, the disassembling needle comprises two C-channels, each having two longitudinal edges that extend from its proximal end to its distal end. The two C-channels mechanically interlock along their longitudinal edges to form the disassembling needle having a lumen disposed therein. In accordance with an embodiment of the present invention, the two C-channels have complementary features that reversibly interlock by a longitudinal movement to form two opposing seams, and which may be separated with or without mechanical assistance.

In accordance with the foregoing embodiments, the disassembling needle simplifies the steps (relative to the basic Seldinger technique) to insert a device percutaneously, and allows for catheters to be preloaded onto the guidewire.

BRIEF DESCRIPTION OF THE SEVERAL VIEWS OF THE DRAWINGS

These and other features, aspects and advantages of various embodiments of the present invention will become better understood with regard to the following description, appended claims, and accompanying drawings where:

FIGS. 11G-11J show additional perspective views of the offset hinged disassembling needle of FIGS. 11A and 11B, shown in its assembled state;

FIGS. 12G-12J show additional perspective views of the perpendicular hinged breakaway needle embodiment of FIGS. 12A and 12B, shown in its assembled state;

FIGS. 12K-12N show additional perspective views of the perpendicular hinged breakaway needle embodiment of FIGS. 12A and 12B, shown in its assembled state;

FIGS. 14C-14F show additional perspective views of the second user-assisted sliding hinged disassembling needle of FIGS. 14A and 14B, shown in its assembled state;

FIGS. 14G-14J show additional perspective views of the second user-assisted sliding hinged disassembling needle of FIGS. 14A and 14B, shown in its assembled state;

FIGS. 14K-14N show additional perspective views of the second user-assisted sliding hinged disassembling needle of FIGS. 14A and 14B, shown in its assembled state;

The accompanying drawings numbered herein are given by way of illustration only and are not intended to be limitative to any extent. Commonly used reference numbers identify the same or equivalent parts of the claimed invention throughout the accompanying drawings.

DETAILED DESCRIPTION

Figure 1:
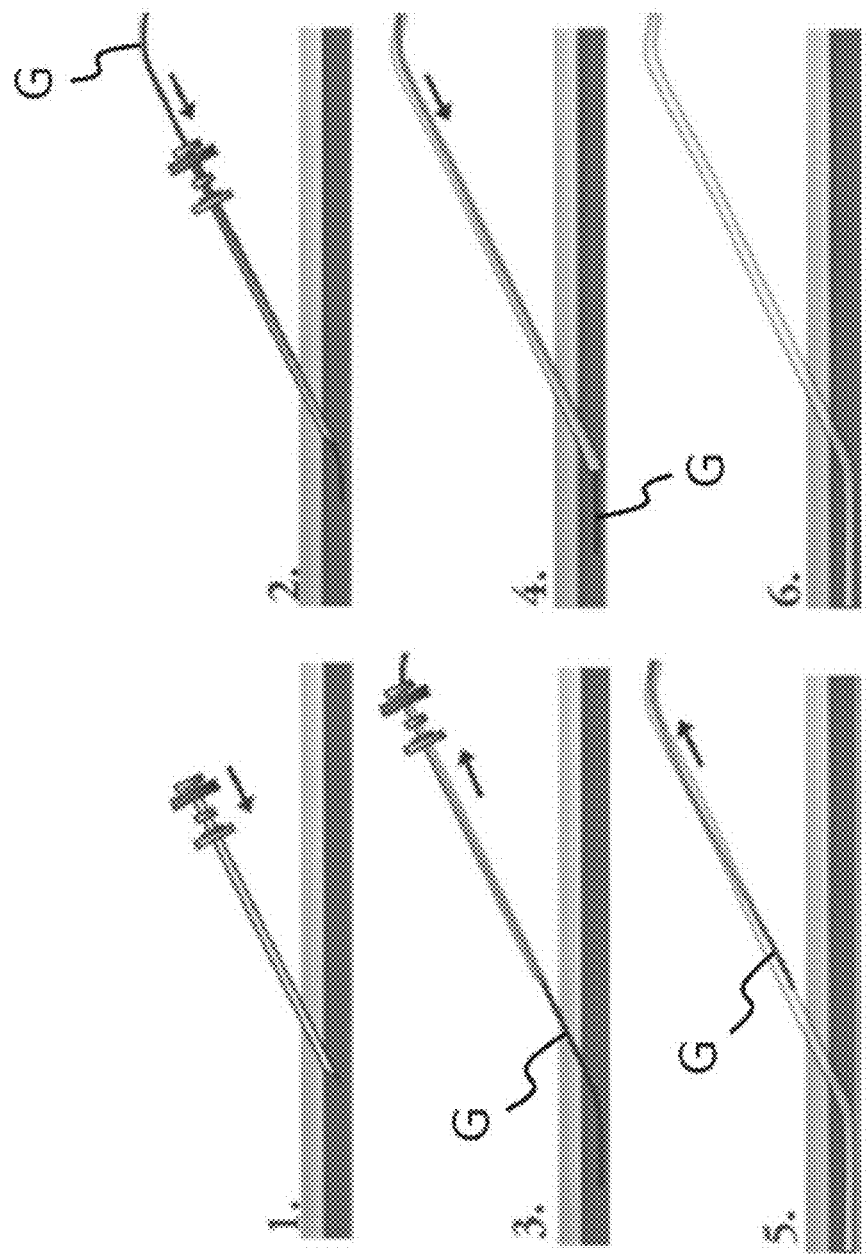
FIG. 1 is a diagram showing a prior art version of the Seldinger technique for percutaneous introduction.
Figure 2:
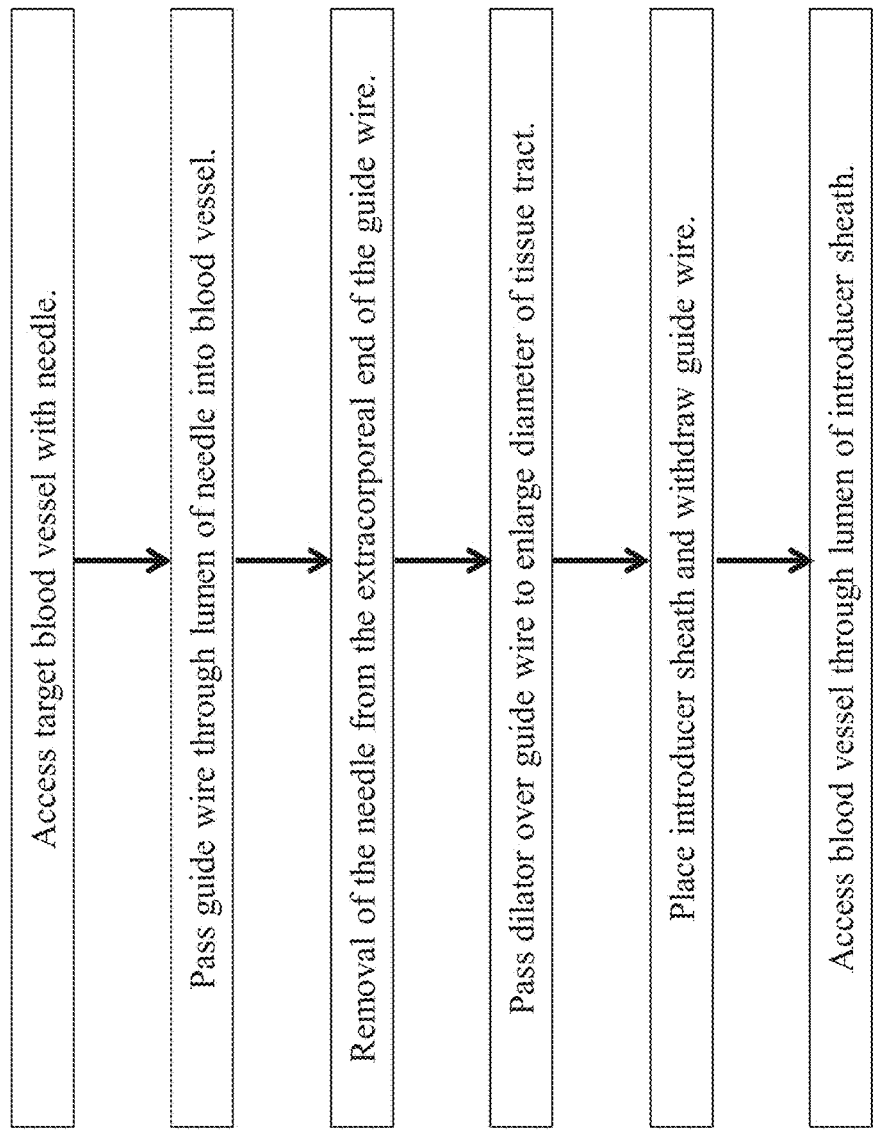
FIG. 2 is a flowchart of the Seldinger technique steps of the prior art.
Figure 3:
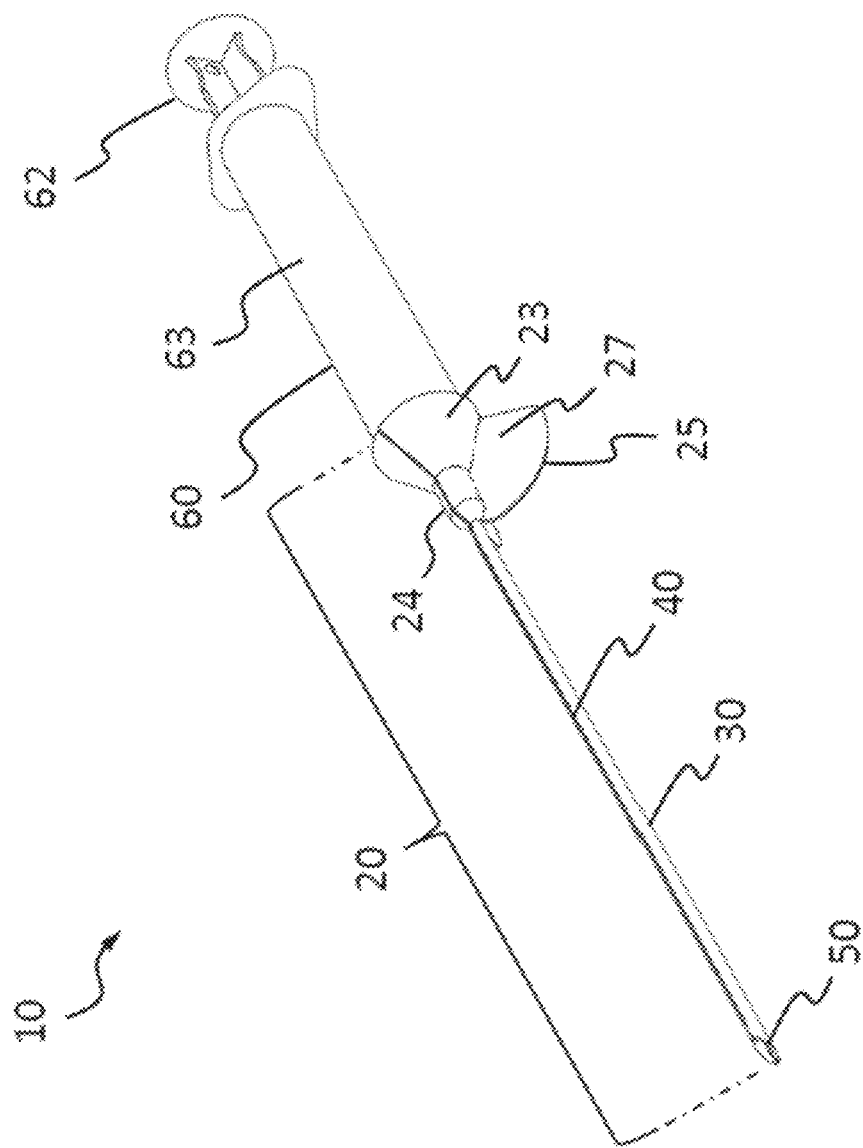
FIG. 3 is a perspective view of a first embodiment of the vascular access disassembling needle, including a syringe, according to an embodiment of the present invention.

FIG. 3 is a perspective view of a first embodiment of a vascular access disassembling needle assembly 10 according to the invention. The disassembling needle assembly 10 comprises a disassembling needle 20 engageable with a syringe 60. In one version, the disassembling needle 20 includes a conical collar 23 and a female docking portion 24 at a proximal end. Two wings 25 extend from both the conical collar 23 and female docking portion 24. The wings 25 are squeezed together by the physician or surgeon to apply sufficient force to split the disassembling needle 20 along its length for rapid removal during a guide wire procedure.

A longitudinal cylindrical needle shaft 30 extends from the female docking portion 24 and serves as the primary structural member supporting percutaneous introduction of the disassembling needle 20 through the epidermis of a subject. A separation seam 40 runs longitudinally along the length of one side of the needle shaft 30 of the disassembling needle 20. An opposing bendable seam 45 (shown in FIG. 7A) runs longitudinally along the length of the needle shaft 30 opposite the separation seam 40. The needle shaft 30 includes a sharp beveled tip 50 at a distal end for puncturing epidermal tissue and obtaining initial percutaneous vascular access.

The syringe 60 may be of the types commonly used in medical procedures, comprising a plunger 62, a barrel 63, and a male docking portion that engages within the female docking portion 24 of the disassembling needle 20. Specific means of engagement between the disassembling needle 20 and the syringe 60 may be accomplished by the use of Luer connections, including the locking and slipping varieties. Luer lock fittings are securely joined by means of a tabbed hub on a female fitting which screws into threads in a sleeve on a male fitting. The Luer slip fittings conform to Luer taper dimensions and are pressed together and held by friction (they have no threads). These Luer engagement components are manufactured from either metal or plastic.

Figure 4:
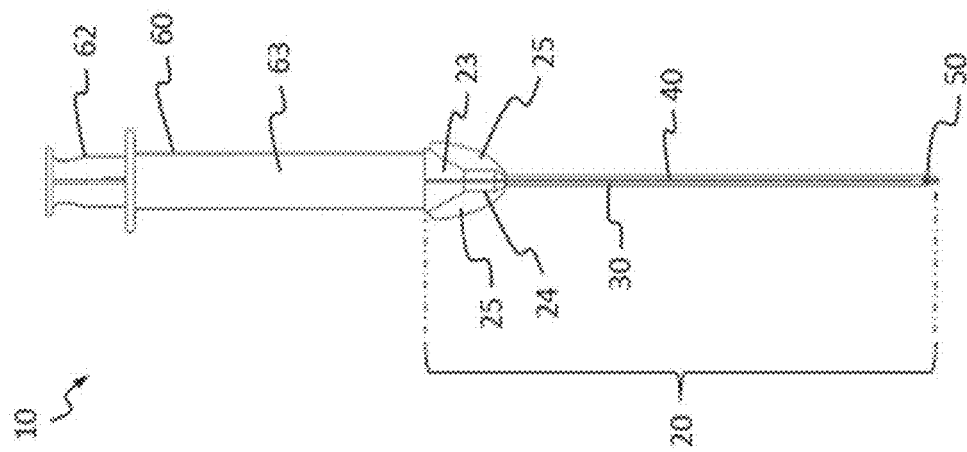
FIG. 4 is a front elevation view thereof.

FIG. 4 is a side elevation view of the disassembling needle assembly 10 shown in FIG. 3. The disassembling needle 20 may be made of stainless steel tubing, nitinol, plastic, or other materials sufficiently rigid to allow percutaneous insertion.

Figure 5:
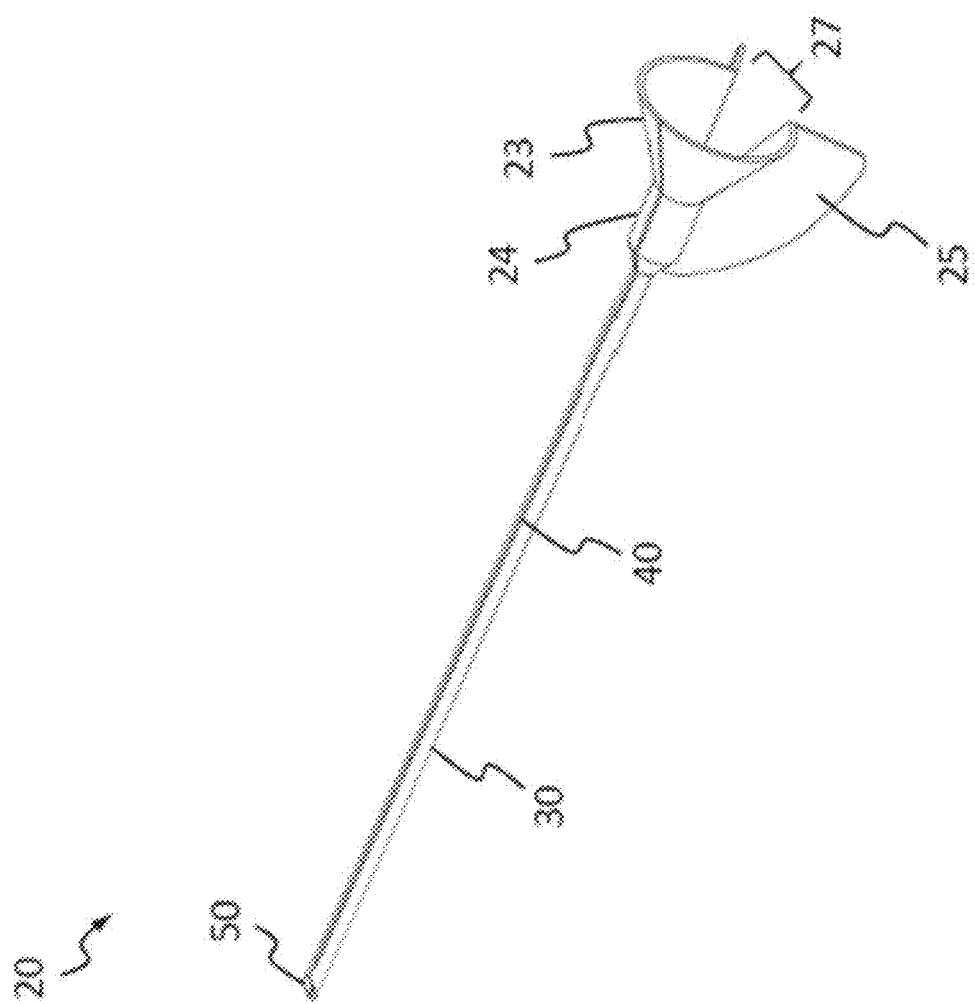
FIG. 5 is a perspective view of the disassembling needle of FIG. 3 in an unsplit state.

FIG. 5 is an alternative perspective view of the disassembling needle 20 disengaged from the syringe 60. The disassembling needle 20 includes a closure gap 27 between the wings 25 of the disassembling needle 20. The closure gap 27 allows the wings 25 to be compressed against each other to apply sufficient force to split the disassembling needle 20 along its separation seam 40.

Figure 6:
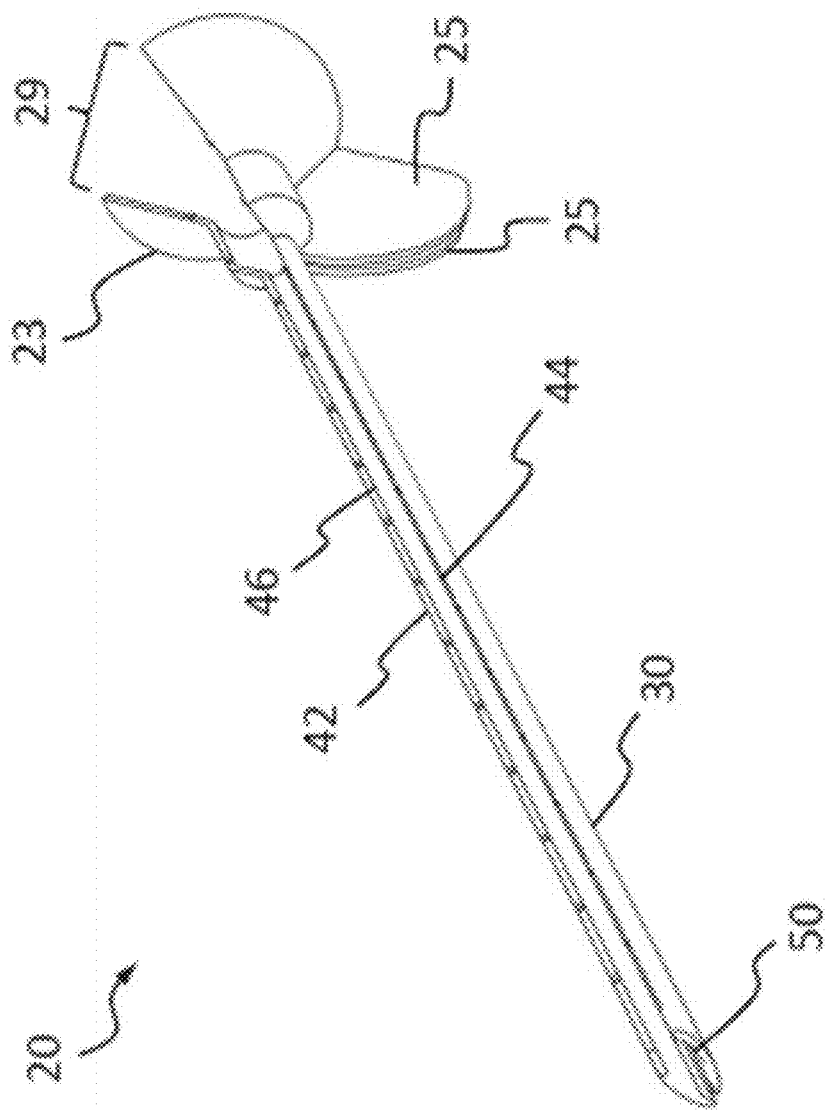
FIG. 6 is a perspective view of the disassembling needle of FIG. 3 in an open, split state.

Turning to FIG. 6, a perspective view of the disassembling needle 20 in an open or split state is shown. When split, the wings 25 have been squeezed together and pressed against one another, causing the separation seam 40 to split, creating two edges 42, 44 and a longitudinal open channel 46 throughout the extent of the disassembling needle 20. The open channel 46 allows the disassembling needle 20 to be removed directly off the guidewire. As shown, the disassembling needle 20 is actuated when the wings 25 are pressed together, closing the closure gap 27 and creating a new opposing opening gap 29. In the actuated open or split state, the new opening gap 29 is opposite the compressed wings 25.

Figures 7A, 7B:
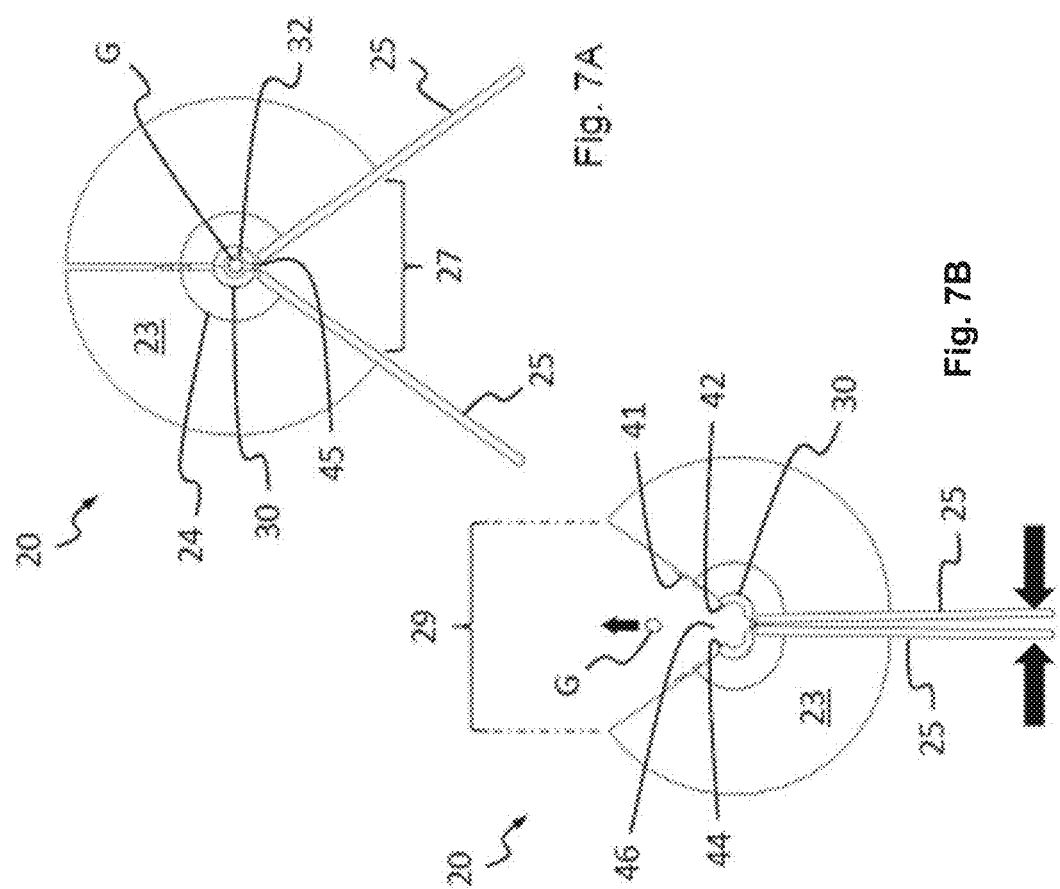
FIG. 7A is a bottom plan view of the disassembling needle of FIG. 3 in an unsplit state.
FIG. 7B is a bottom plan view of the disassembling needle of FIG. 3 in an open split state.

FIGS. 7A and 7B provide end views of the disassembling needle 20 in an original closed state and open state. FIG. 7A is an illustration of the disassembling needle 20 in an original, unbroken, or closed state; FIG. 7B is an illustration of the disassembling needle 20 in an open, split state. In a closed state, as illustrated in FIG. 7A, the disassembling needle 20 is able to receive a guide wire G deployed within a lumen 32 of the needle shaft 30. A bendable seam 45 runs along the length of the needle shaft 30 and the female docking portion 24, positioned between the ends of the two wings 25 adjacent the needle shaft 30. When the needle 20 is actuated, as illustrated in FIG. 7B, the wings 25 are pressed together, pivoting on the hinge functionality associated with the bendable seam 45, causing the separation seam 40 to split. The closure gap 27 (or closure angle) between the two wings 25 is sized such that when the two wings 25 are pressed together, the new opening gap 29 between the edges 42, 44 of the split portion of the needle shaft 30 is sufficient to allow the disassembling needle 20 to be easily removed off the guide wire G. In other words, the two wings 25 are separated by an angle large enough to provide a vertical angle in the new opening gap 29 in the separation seam 40 sufficient to enable removal of the vascular access disassembling needle off the guide wire G having a thickness T.

Figures 8A, 8B, 8C:
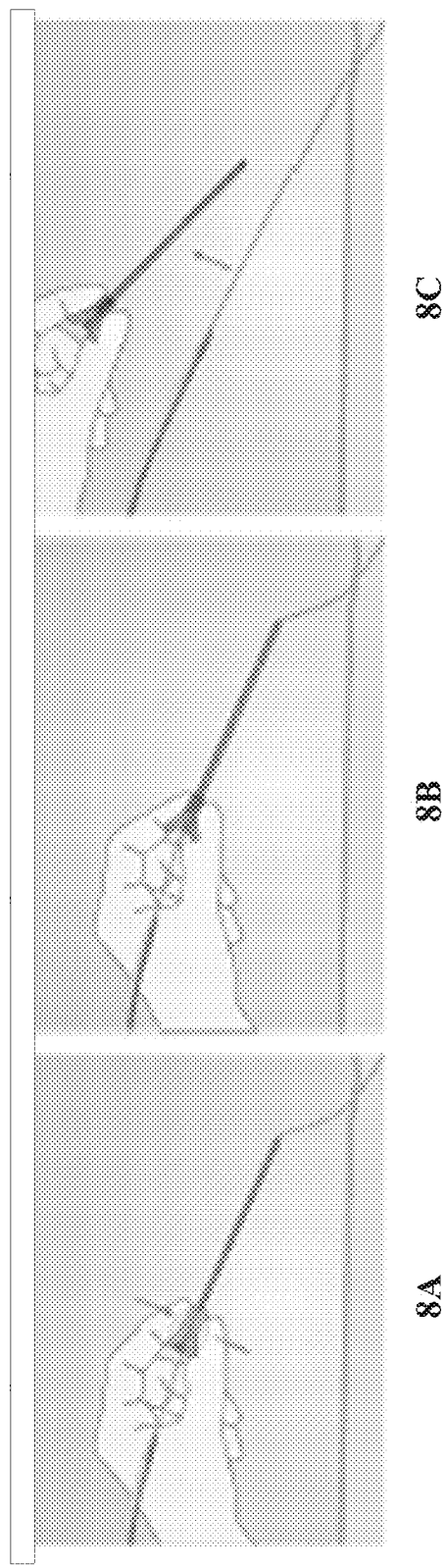
FIGS. 8A-8C are diagrams illustrating a method for disassembling the needle of FIG. 3 according to an embodiment of the present invention.

FIGS. 8A, 8B, and 8C illustrate three typical steps associated with disassembling the disassembling needle 20. In FIG. 8A, a hand of a user is shown grasping two wings 25 of the disassembling needle 20 with the index and thumb ends applying a compression force (indicated by the directional arrows). In FIG. 8B, two wings 25 are shown in a compressed configuration, where new opening gap 29 and open channel 46 into lumen 32 are shown. And in FIG. 8C, the disassembling needle 20 is shown removed from a guide wire G after having been displaced from lumen 32 via new opening 29 and open channel 46.

Figure 9:
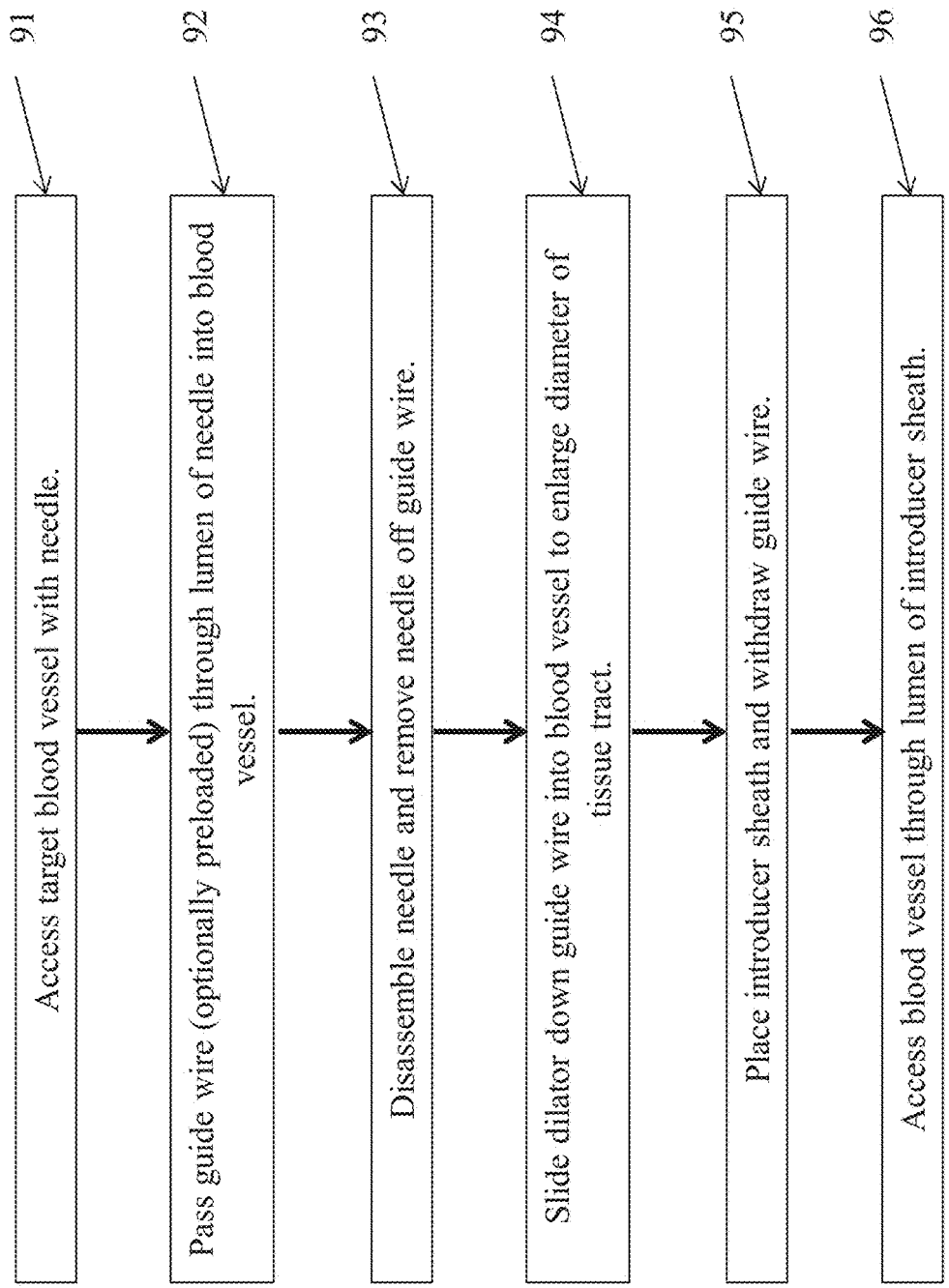
FIG. 9 is a flowchart showing a general method for percutaneous introduction using a disassemblable needle, in accordance with an embodiment of the present invention.

Referring now to FIG. 9 and with further reference to FIG. 4, beginning at step 91, with a syringe 60 engaged with the disassembling needle 20, a surgeon (or emergency responder) inserts the beveled tip 50 of the disassembling needle 20 through the subject's epidermis and into the target blood vessel. The surgeon may ensure proper access in the target vascular region has been achieved by slightly withdrawing the syringe plunger 62 to withdraw a small quantity of blood into the barrel 63 of the syringe 60. Afterwards, the surgeon removes the syringe 60 from the disassembling needle 20. At step 92, the surgeon inserts a guide wire G through the conical collar 23 and into the lumen 32 of the needle shaft 30 of the disassembling needle 20 to pass into the target vascular region. The conical collar 23 acts as a funnel to guide a tip of the guide wire G into the lumen 32 of the needle shaft 30. Because the needle 20 is disassemblable, the guidewire G may be preloaded with additional devices, such as a dilator or introducer sheath.

The surgeon withdraws the disassembling needle 20 from the entry site while the guide wire G remains in place. With the disassembling needle 20 fully withdrawn, at step 93, the surgeon disassembles the needle 20 and removes the needle 20 off the guidewire G. In the embodiment shown in FIGS. 3-8, the surgeon grasps the two wings 25 of the disassembling needle 20 in preparation for compression of the two wings 25. The conical collar 23 and two wings 25 are preferably shaped to provide the surgeon with a secure grip on the two wings 25 when pressing the two wings 25 together to split the disassembling needle 20. The taper of the conical collar 23 and the angular departure of the two wings 25 create a pocket 27 (see FIG. 5) that accommodates the surgeon's thumb and index finger. Although shown in FIG. 8 as being actuated using a left hand, the disassembling needle 20 may be rotated to support actuation using the surgeon's right hand. The shape of the two wings 25 and conical collar 23 may be varied to provide different finger pocket 27 shapes. The two wings 25 and conical collar 23 may include ridges or other raised or roughened features to enhance the surgeons grasp on the two wings 25 of the disassembling needle 20 when splitting the longitudinal cylindrical needle shaft 30. The two wings 25 and conical collar 23 may also be coated in material, such as rubber, to enhance the surgeon's grasp while splitting the disassembling needle 20.

As the surgeon squeezes the wings 25 together, a separation force is applied to the separation seam 40, thereby causing it to split to form an open channel 46, which has been created along the entire length of the longitudinal cylindrical needle shaft 30. Accordingly, it is advantageous that separation seam 40 comprise a line of weakness, yet maintains fluid integrity up to the time of separation. In an embodiment, the separation seam 40 may be formed by an adhesive bond along the longitudinal edges and/or a film coating, such as a thin (e.g., about 5 microns to about 1 mm) polymer coating. In another embodiment, separation seam 40 is formed by a mechanical interference junction along the longitudinal edges. The disassembling needle 20 may be easily removed off the guide wire G to allow other procedures to be implemented using the guide wire G. For example, at step 94, the surgeon may slide a dilator, which may be preloaded onto the guidewire, along the guide wire G and into the target blood vessel to enlarge diameter of tissue tract. At step 95, the surgeon may then place an introducer sheath and withdraw the guidewire G. At step 96, the surgeon is then able to deploy other medical devices into the target blood vessel region through the lumen of the introducer sheath.

While the foregoing process shown in FIG. 9 has been described in reference to the disassembling needle 20 shown in FIGS. 3-8, the process is not limited thereto. A common aspect to each of the following embodiments described below is the separation of the longitudinal cylindrical needle shaft to open the lumen therein thereby creating an egress pathway for the guide wire G.

Figures 10A, 10B:
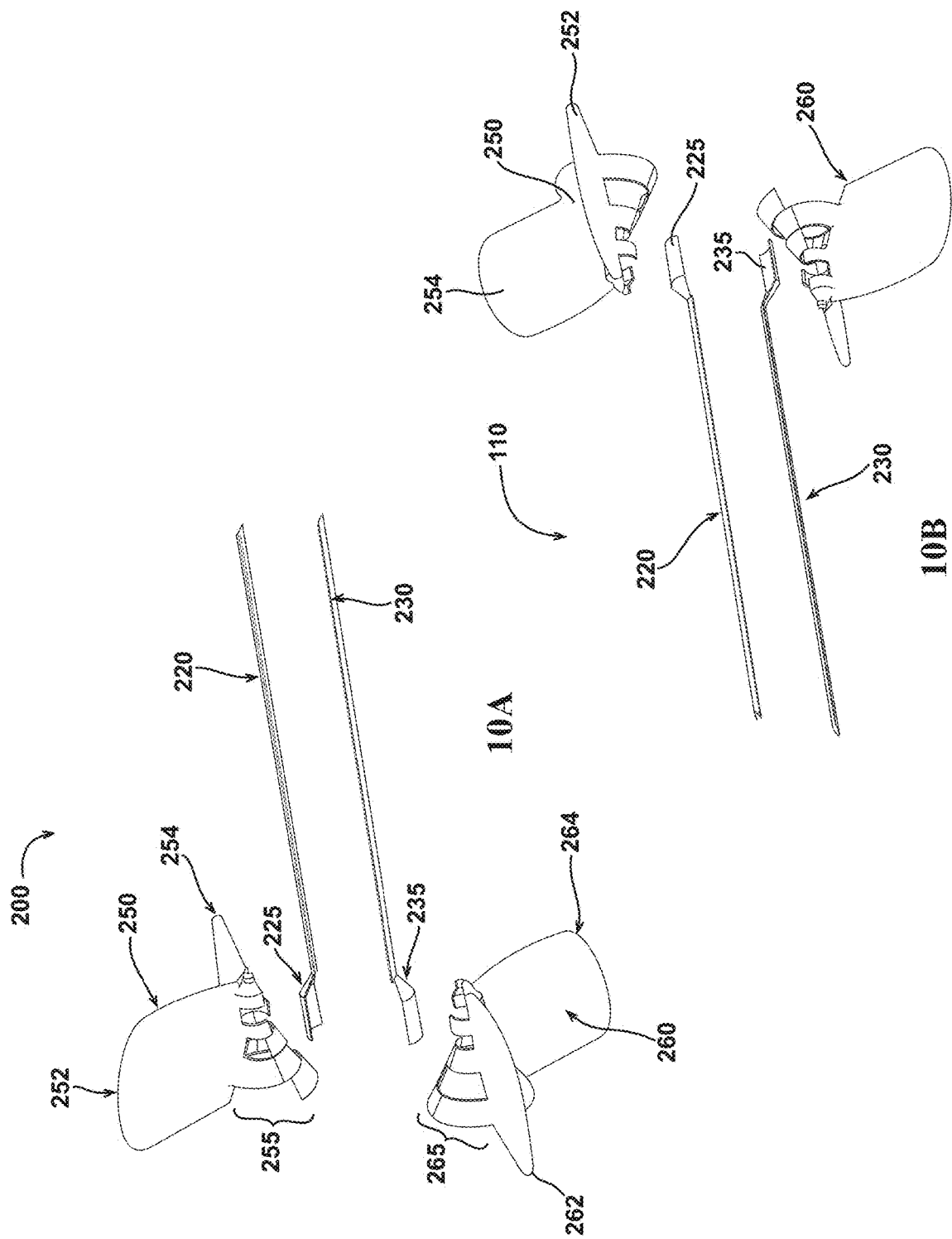
FIGS. 10A and 10B show two complementary perspective views of a dual hinged disassembling needle embodiment, where the components of this embodiment are shown in exploded states.
Figures 10C, 10D, 10E, 10F:
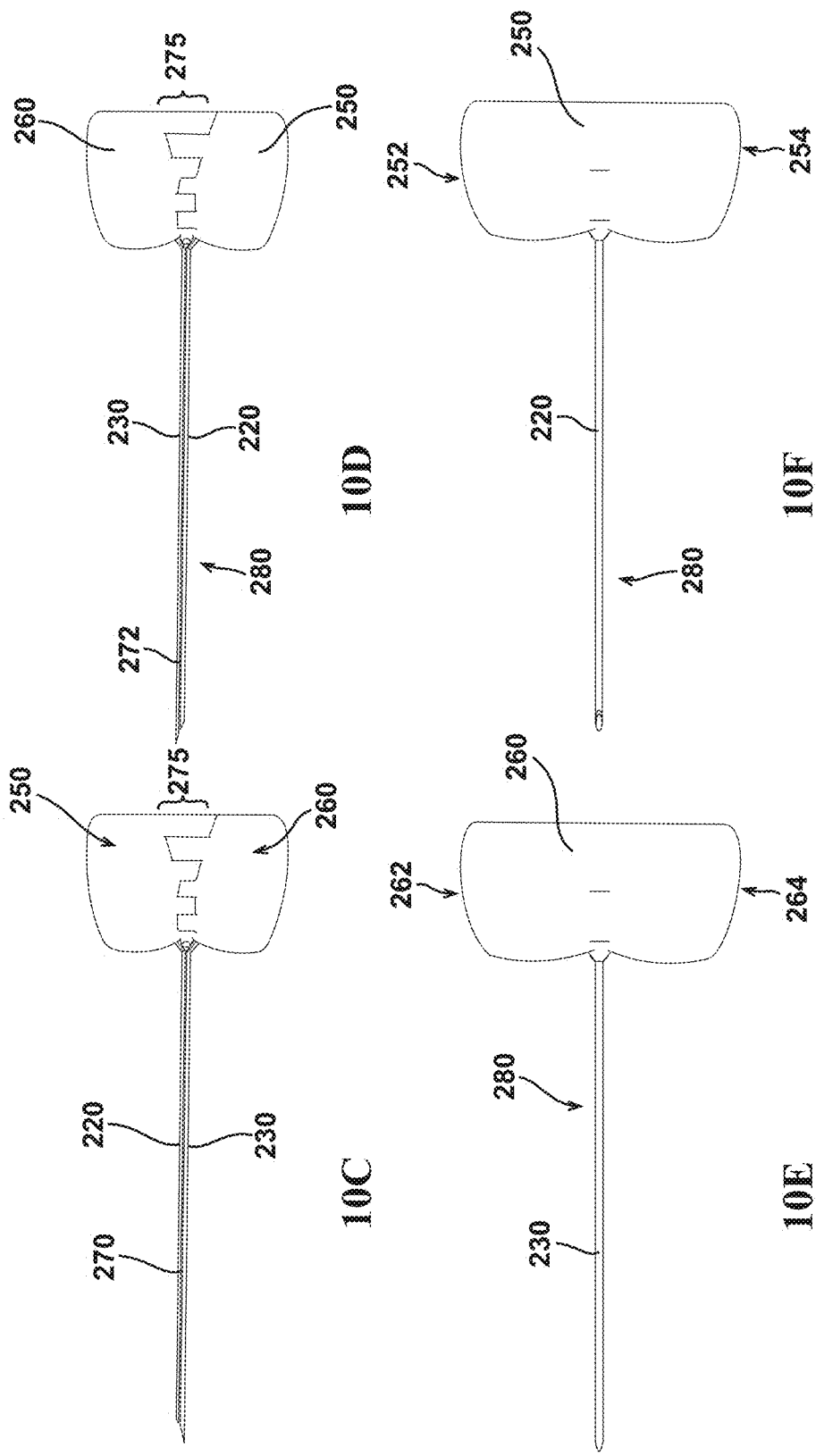
FIGS. 10C-10F show additional perspective views of the dual hinged disassembling needle of FIGS. 10A and 10B, shown in its assembled state.
Figures 10G, 10H, 10I, 10J:
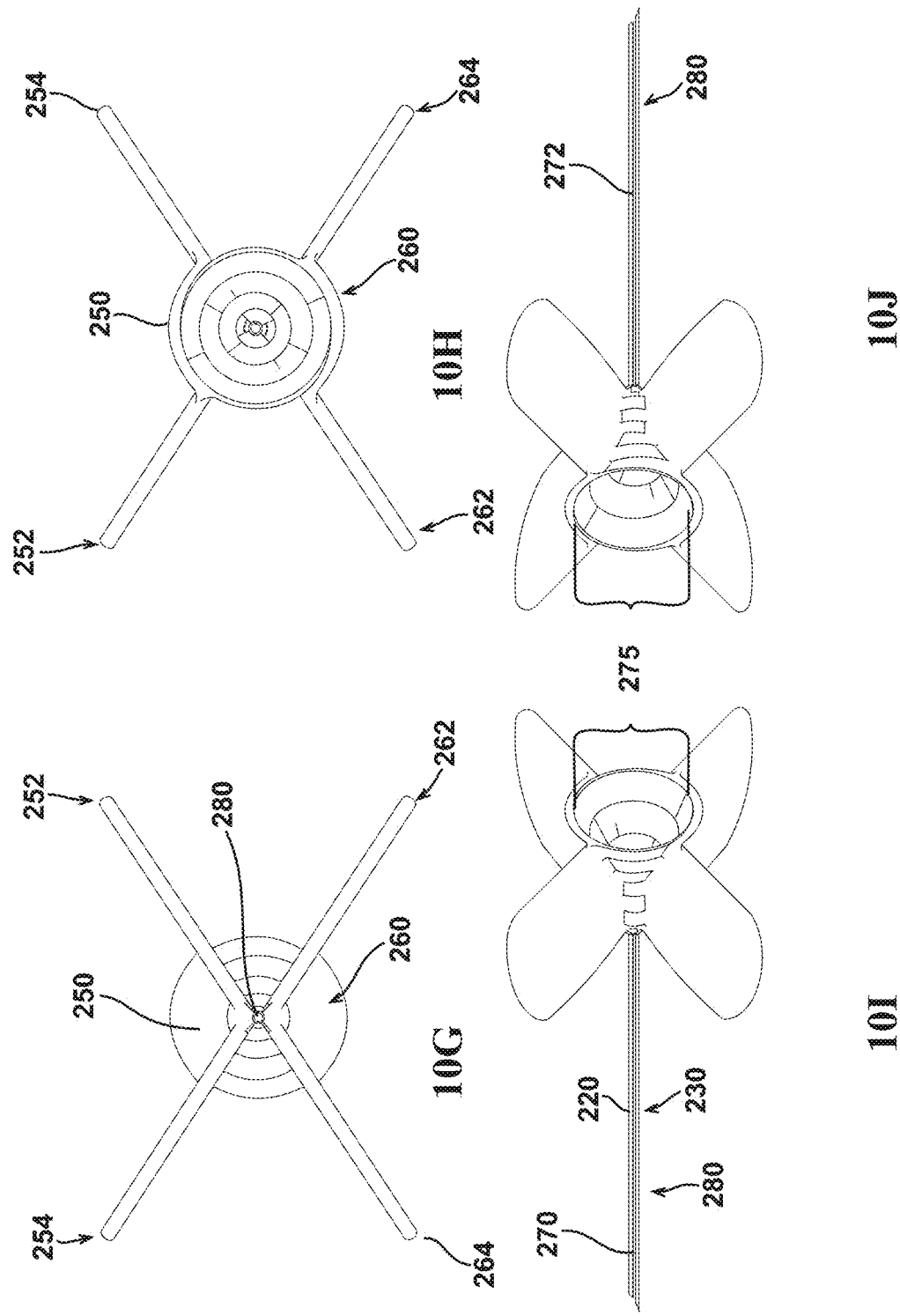
FIGS. 10G-10J show additional perspective views of the dual hinged disassembling needle of FIGS. 10A and 10B, shown in its assembled state.
Figure 10K:
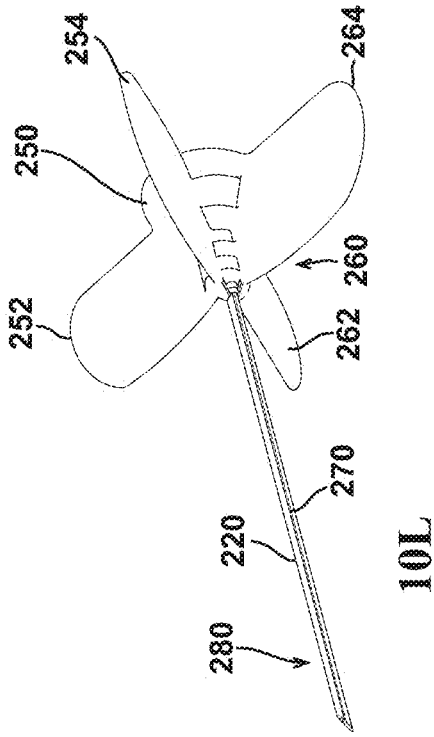
FIGS. 10K-10N show additional perspective views of the dual hinged disassembling needle of FIGS. 10A and 10B, shown in its assembled state.
Figure 10L:
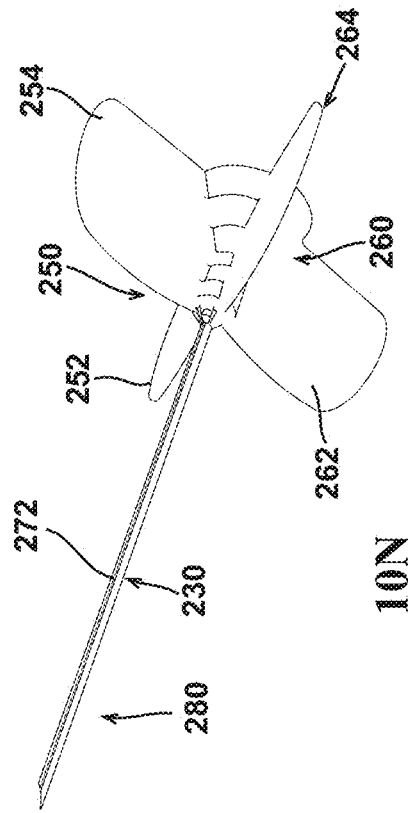
Figure 10M:
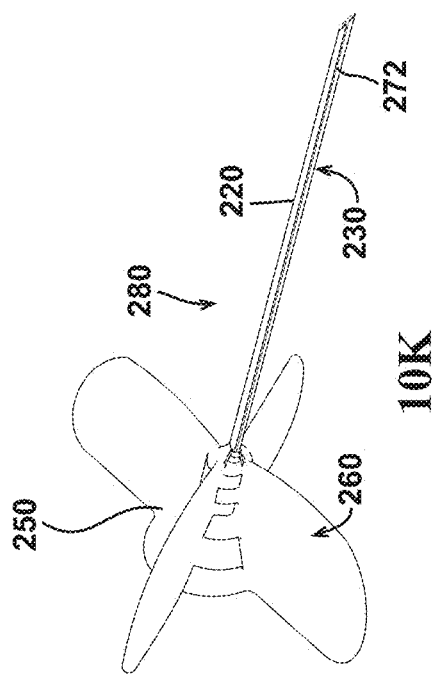
Figure 10N:
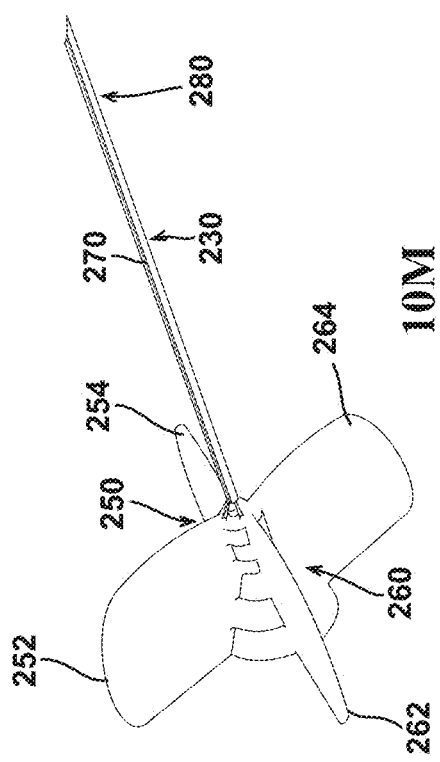

FIGS. 10A-10N show various plain and perspective views of a dual hinged disassembling needle 200, where FIGS. 10A and 10B show the components of this embodiment in two complementary exploded states. More specifically, the dual hinged disassembling needle 200 includes two interlocking halves 250, 260 with each having two perpendicularly-extending tabs per half. A first interlocking half 250 includes two tabs 252, 254 and a second interlocking half includes two tabs 262, 264. Each of the first and second interlocking halves 250, 260 are connected to its respective needle shaft halves 220, 230 by a collar segment 255, 265 that mates with or affixes to extension members 225, 235. The assembly of the two interlocking halves 250, 260 onto the extension members 225, 235 creates a conical receiver 275 that accepts a syringe and a longitudinal cylindrical needle 280 that accepts a guidewire. The tabs (252, 254, 262, or 264) and collar segments 255, 265 may include ridges or other raised or roughened features to enhance the surgeons grasp on the wings (252, 254, 262, or 264) of the disassembling needle 200 when splitting the longitudinal cylindrical needle 280. The tabs (252, 254, 262, or 264) and collar segments 255, 265 may also be coated in material, such as rubber, to enhance the surgeon's grasp while splitting the disassembling needle 200. Disassembly of the needle 200 into two halves 220, 230 is achieved by compressing the ipsilateral tabs (252, 262 or 254, 264) of each respective half. This enables the interlocking halves to slide off of each other and allows for separation of at least one of the contralateral seams 270 (FIG. 10C) and 272 (FIG. 10D) in the shaft 280 of the needle 200. FIGS. 10C and 10D show the assembled state of the disassembling needle 200 from opposing side views, while FIGS. 10E and 10F show the assembled state of the disassembling needle 200 from opposing top and bottom views. FIGS. 10G and 10H show the assembled state of the disassembling needle 200 from a front view and a back view, respectively. FIG. 10I through FIG. 10N show complementary assembled state perspective views of the disassembling needle 200.

Figures 11A, 11B:
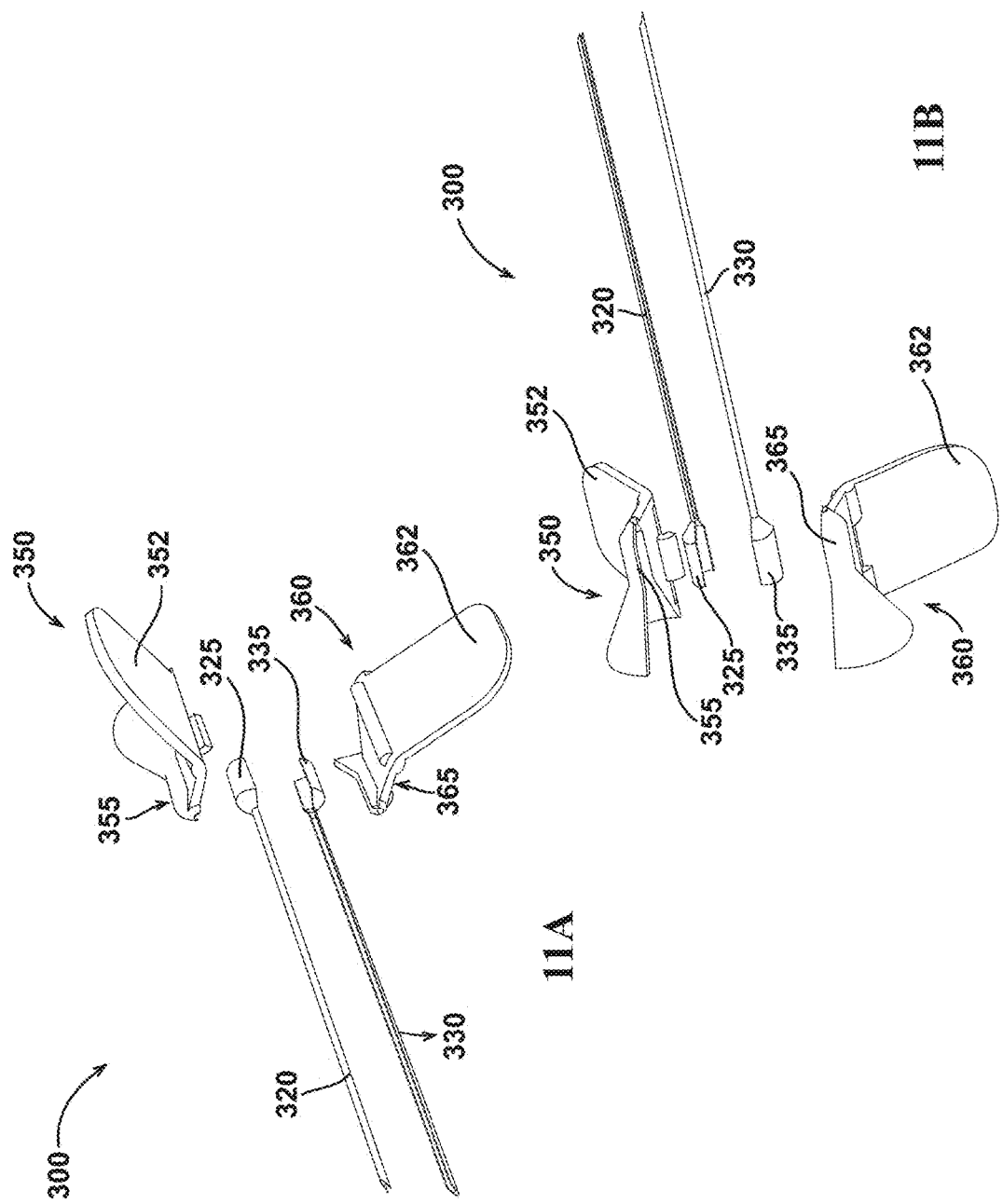
FIGS. 11A and 11B show two complementary perspective views of an offset hinged disassembling needle embodiment, where the components of this embodiment are shown in exploded states.
Figures 11C, 11D, 11E, 11F:
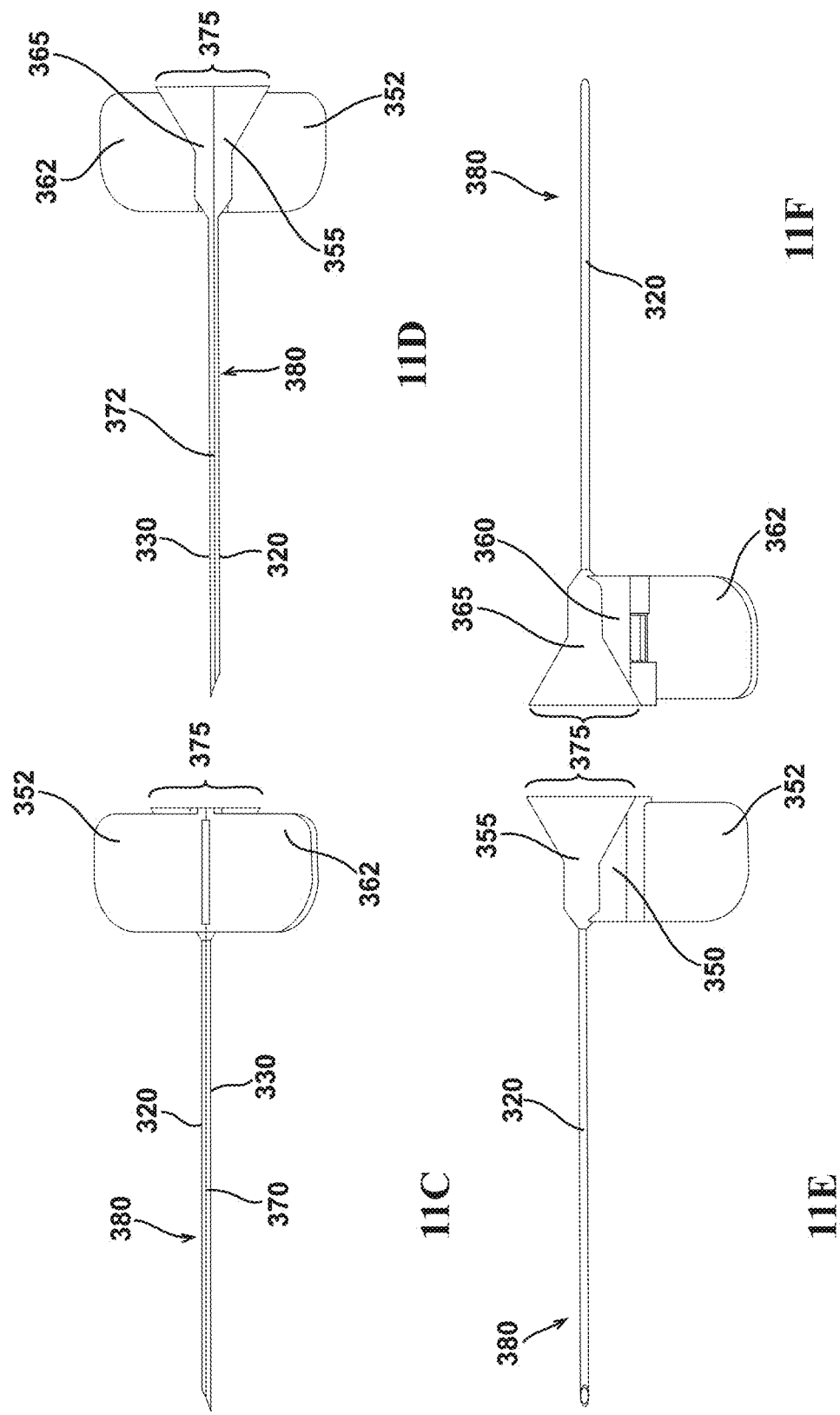
FIGS. 11C-11F show additional perspective views of the offset hinged disassembling needle of FIGS. 11A and 11B, shown in its assembled state.
Figures 11K, 11L, 11M, 11N:
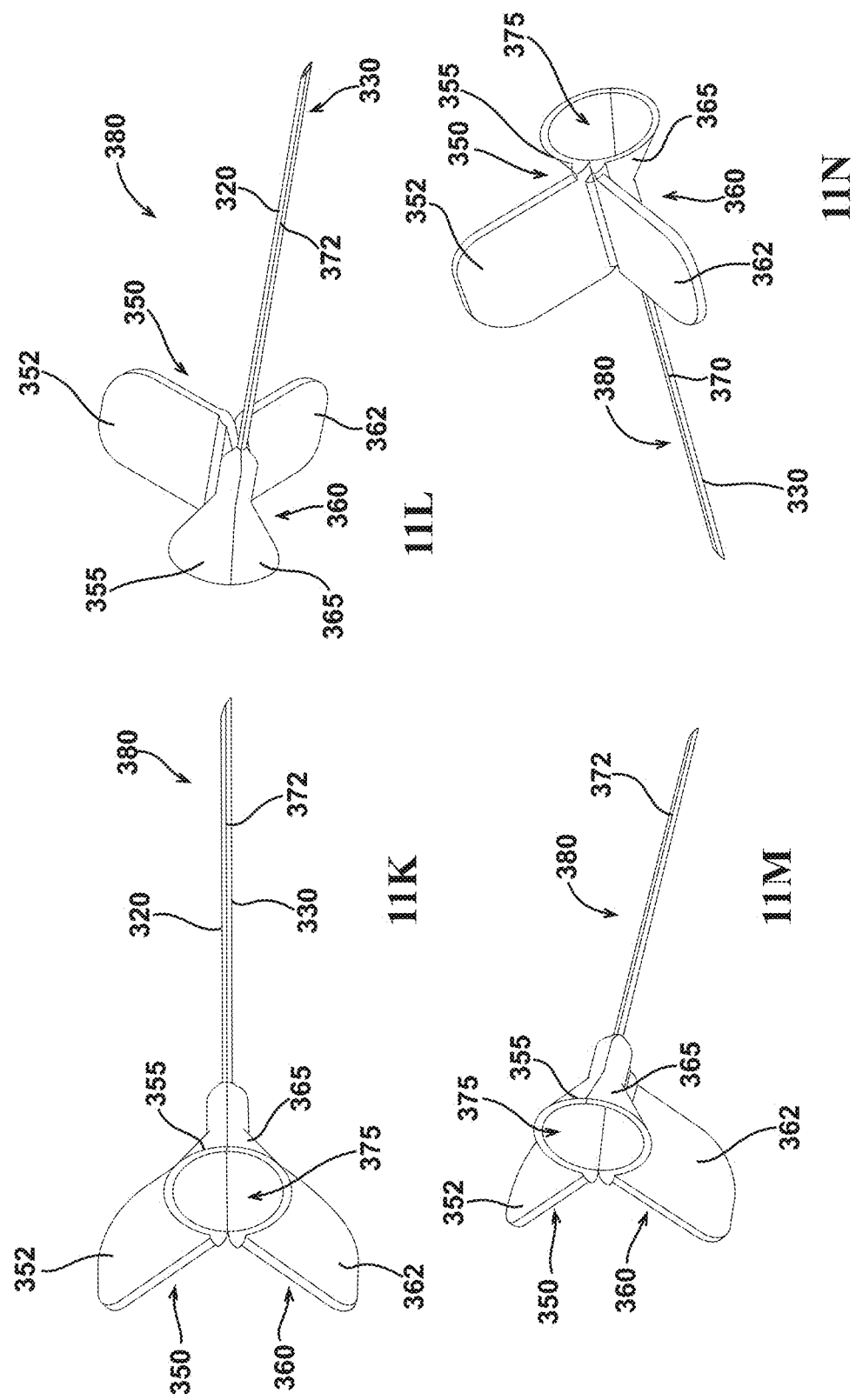
FIGS. 11K-11N show additional perspective views of the offset hinged disassembling needle of FIGS. 11A and 11B, shown in its assembled state.

FIGS. 11A-11N show various plane and perspective views of an offset hinged disassembling needle 300, where FIGS. 11A and 11B show the components of this embodiment in two complementary exploded states. More specifically, the offset hinged disassembling needle 300 includes two interlocking halves 350, 360 with each having a perpendicularly-extending tab per half. A first interlocking half 350 includes a tab 352 and a second interlocking half 360 includes a tab 362. Each of the first and second interlocking halves 350, 360 are connected to its respective needle shaft halves 320, 330 by a collar segment 355, 365 that mates with or affixes to extension members 325, 335. The assembly of the two interlocking halves 350, 360 onto the extension members 325, 335 creates a conical receiver 375 that accepts a syringe and a longitudinal cylindrical needle 380 that accepts a guidewire. The tabs (352, 362) and collar segments 355, 365 may include ridges or other raised or roughened features to enhance the surgeons grasp on the tabs (352, 362) of the disassembling needle 300 when splitting the longitudinal cylindrical needle 380. The tabs (352, 362) and collar segments 355, 365 may also be coated in material, such as rubber, to enhance the surgeon's grasp while splitting the disassembling needle 300. Disassembly of the needle 300 into two halves 320, 330 is achieved by compressing the ipsilateral tabs (352, 362) of each respective half. This enables the interlocking halves to slide off of each other and allows for separation of at least one the contralateral seams 370 (FIG. 11C) and 372 (FIG. 11D) in the shaft 380 of the needle 300.

In an embodiment, to effect disassembly of the disassembling needle 300, the tabs 352, 362 are pressed together, pivoting on the hinge functionality associated with the bendable seam 370, causing the separation seam 372 on the side opposite the hinge to split. A closure gap 390 (or angle θ) between the tabs is sufficiently sized such that when the tabs 352, 362 are pressed together, the new opening gap between the edges of the split portion of the needle shaft is sufficiently wide enough to allow the disassembling needle to be easily removed off the guide wire. In an embodiment, the angle θ is about 20 degrees or more, or about 25 degrees or more, or about 30 degrees or more. FIGS. 11C and 11D show the assembled state of the disassembling needle 300 from opposing side views, while FIGS. 11E and 11F show the assembled state of the disassembling needle 300 from opposing top and bottom views, respectively. FIGS. 11G and 11H show the assembled state of the disassembling needle 300 from a front view and a back view, respectively. FIG. 11I through FIG. 11N show complementary assembled state perspective views of the disassembling needle 300.

Figures 12A, 12B:
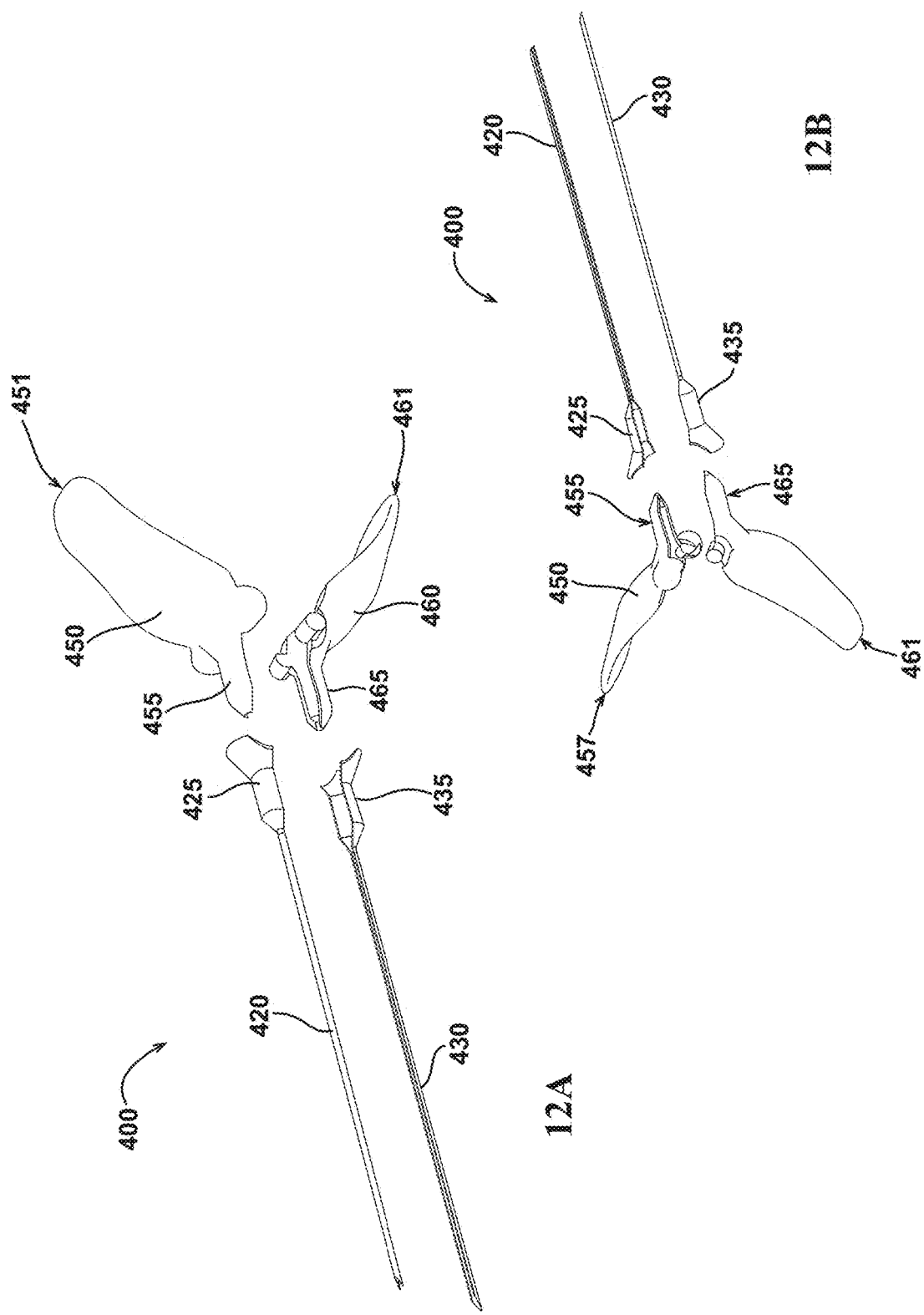
FIGS. 12A and 12B show two complementary perspective views of a perpendicular hinged breakaway needle embodiment, where the components of this embodiment are shown in exploded states.

FIGS. 12A-12N show various plain and perspective views of a perpendicular hinged disassembling needle 400, where FIGS. 12A and 12B show the components of this embodiment in two complementary exploded states. More specifically, the perpendicular hinged disassembling needle 400 includes two halves 450, 460 with each having a longitudinally-extending tab per half. A first half 450 includes a tab 451 and a collar segment 455, and a second half 460 includes a tab 461 and a collar segment 465. The disassembling needle 400 further includes a longitudinal cylindrical needle shaft 480, which is formed by two needle shaft halves 420, 430, each of which having an extension section 425, 435, respectively. The first and second halves 450, 460 are adapted to join together to form a pivot region 495, which acts as a fulcrum during the disassembly of the disassembling needle 400. Their corresponding collar segments 455, 465 join together to form a male extension section 496, which mates with a conical receiver 475 formed by a combination of extensions 425, 435.

Figures 12C, 12D, 12E, 12F:
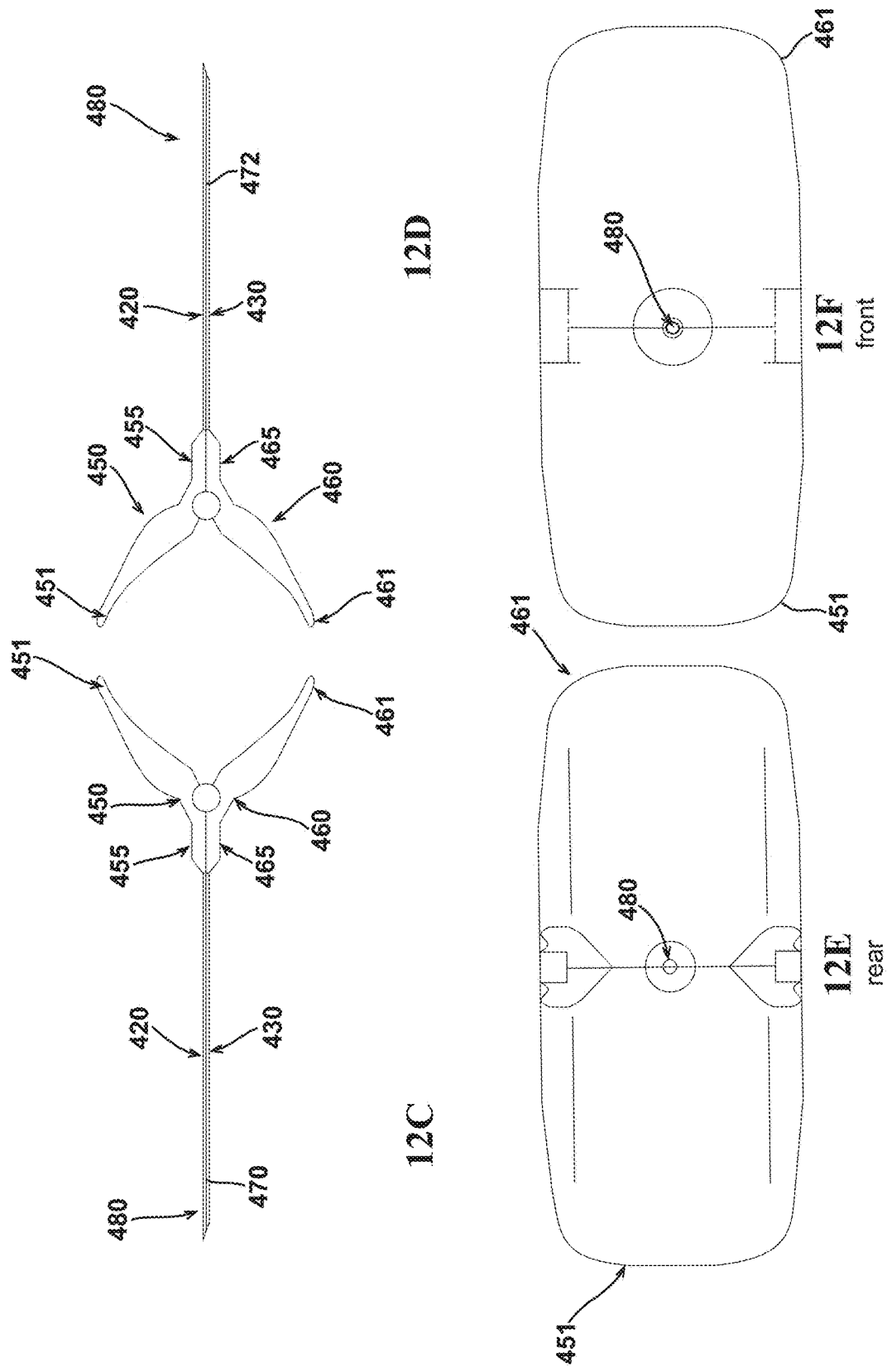
FIGS. 12C-12F show additional perspective views of the perpendicular hinged breakaway needle embodiment of FIGS. 12A and 12B, shown in its assembled state.

The tabs (451, 461) may include ridges or other raised or roughened features to enhance the surgeons grasp on the tabs (451, 461) of the disassembling needle 400 when splitting the longitudinal cylindrical needle 480. The tabs (451, 461) may also be coated in material, such as rubber, to enhance the surgeon's grasp while splitting the disassembling needle 400. Disassembly of the needle 400 into two halves 420, 430 is achieved by compressing the longitudinally-extending tabs (451, 461), which thereby causes the distal end of the collar segments 455, 465 to separate. As the collar segments 455, 465 separate, the force is transferred to the extensions 425, 435, and thereby causes a separation of the contralateral seams 470 (FIG. 12C) and 472 (FIG. 12D) in the longitudinal cylindrical needle shaft 480 of the disassembling needle 400. Accordingly, it is particularly advantageous that contralateral seams 470, 472 comprise lines of weakness. In an embodiment, the contralateral seams 470, 472 may be formed by an adhesive or film. In another embodiment, contralateral seams 470, 472 are formed by a mechanical interference junction of the longitudinal edges of the two halves 420, 430. FIGS. 12C and 12D show the assembled state of the disassembling needle 400 from opposing side views, while FIGS. 12E and 12F show the assembled state of the disassembling needle 400 from opposing top and bottom views, respectively. FIGS. 12G and 12H show the assembled state of the disassembling needle 300 from a front view and a back view, respectively. FIG. 12I through FIG. 12N show complementary assembled state perspective views of the disassembling needle 400.

Figures 13A, 13B:
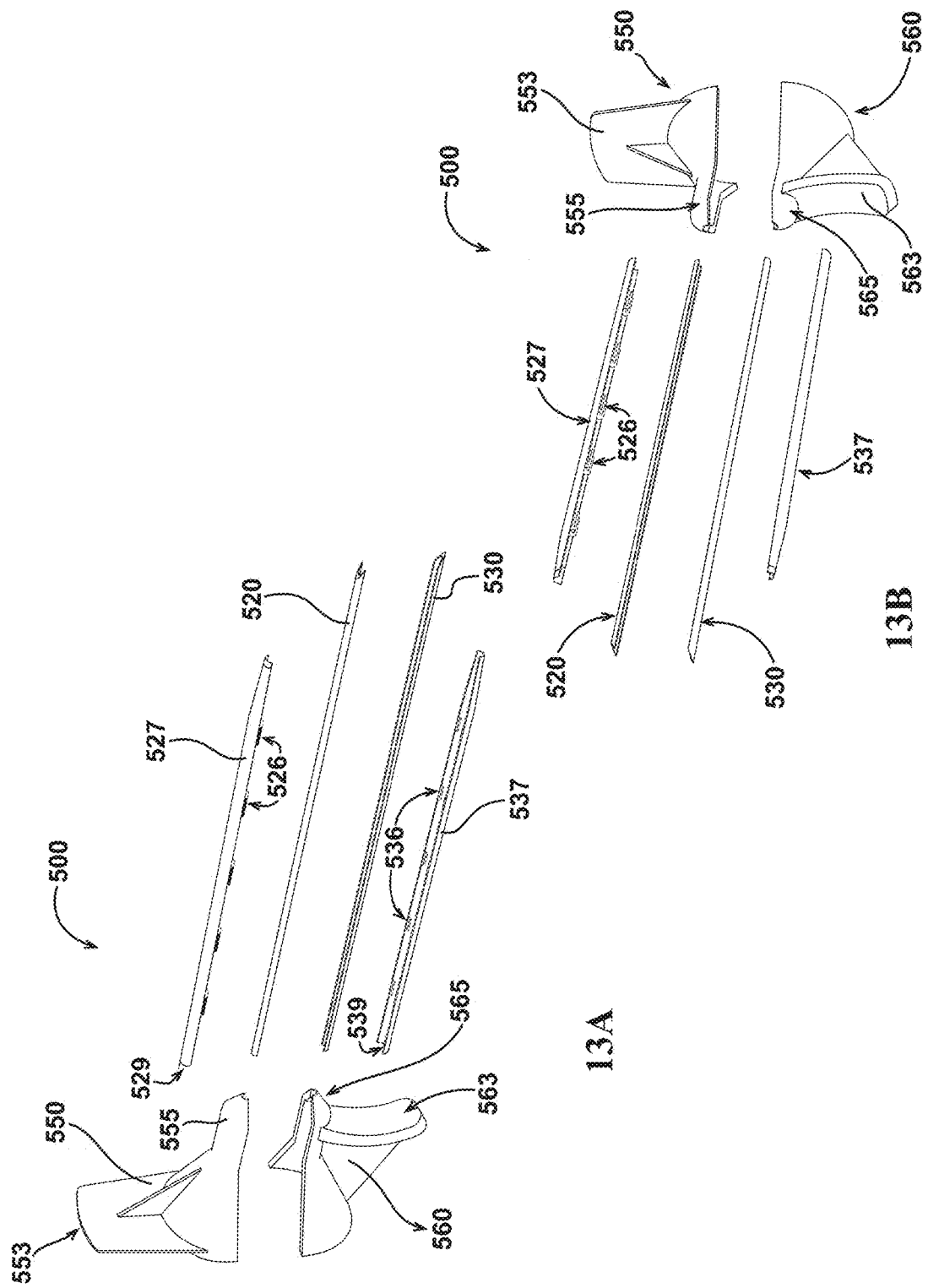
FIGS. 13A and 13B show two complementary perspective views of a first user-assisted sliding disassembling needle embodiment, where the components of this embodiment are shown in exploded states.
Figures 13C, 13D, 13E, 13F:
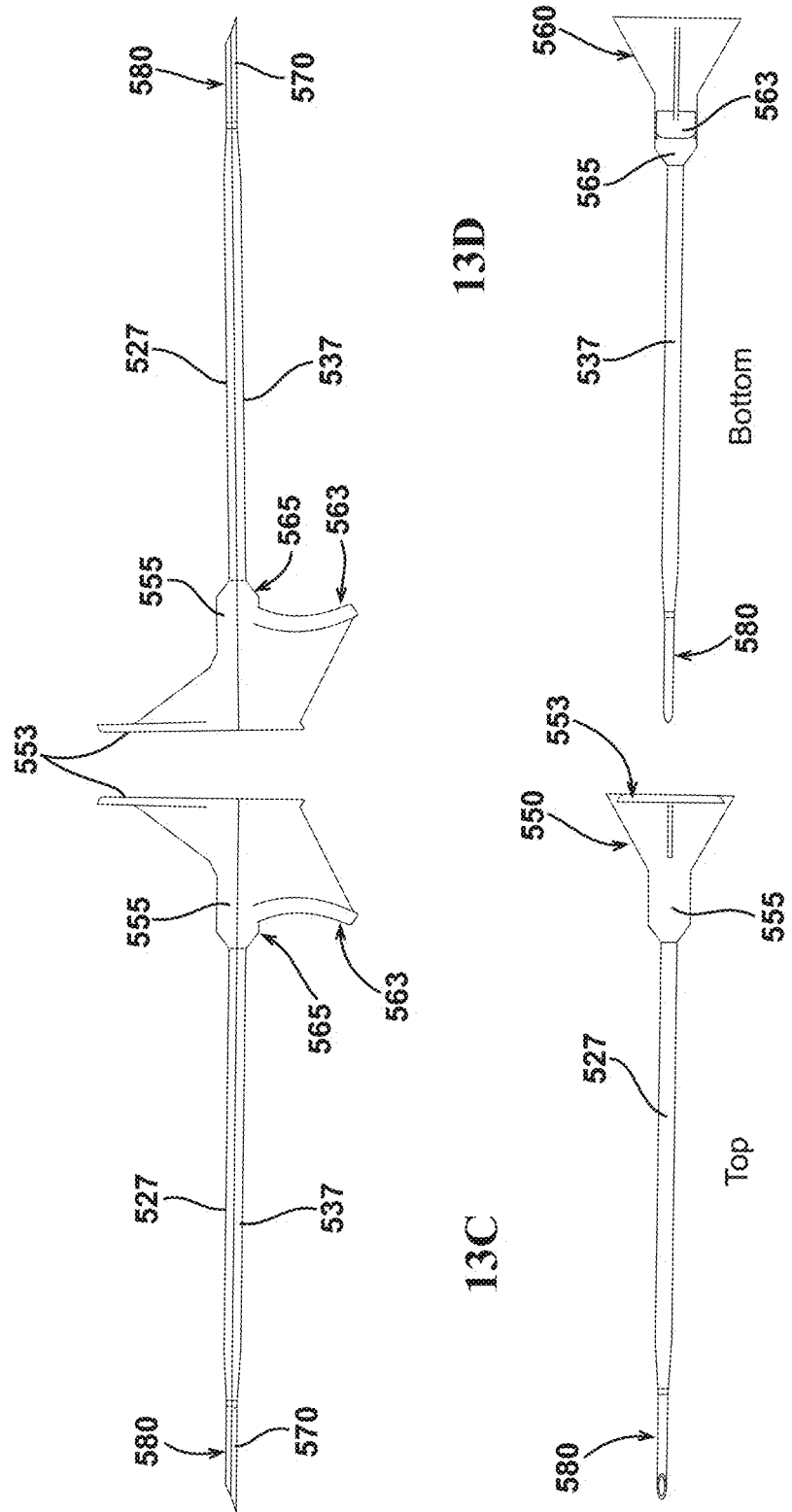
FIGS. 13C-13F show additional perspective views of the first user-assisted sliding hinged disassembling needle of FIGS. 13A and 13B, shown in its assembled state.
Figures 13G, 13H, 13I, 13J:
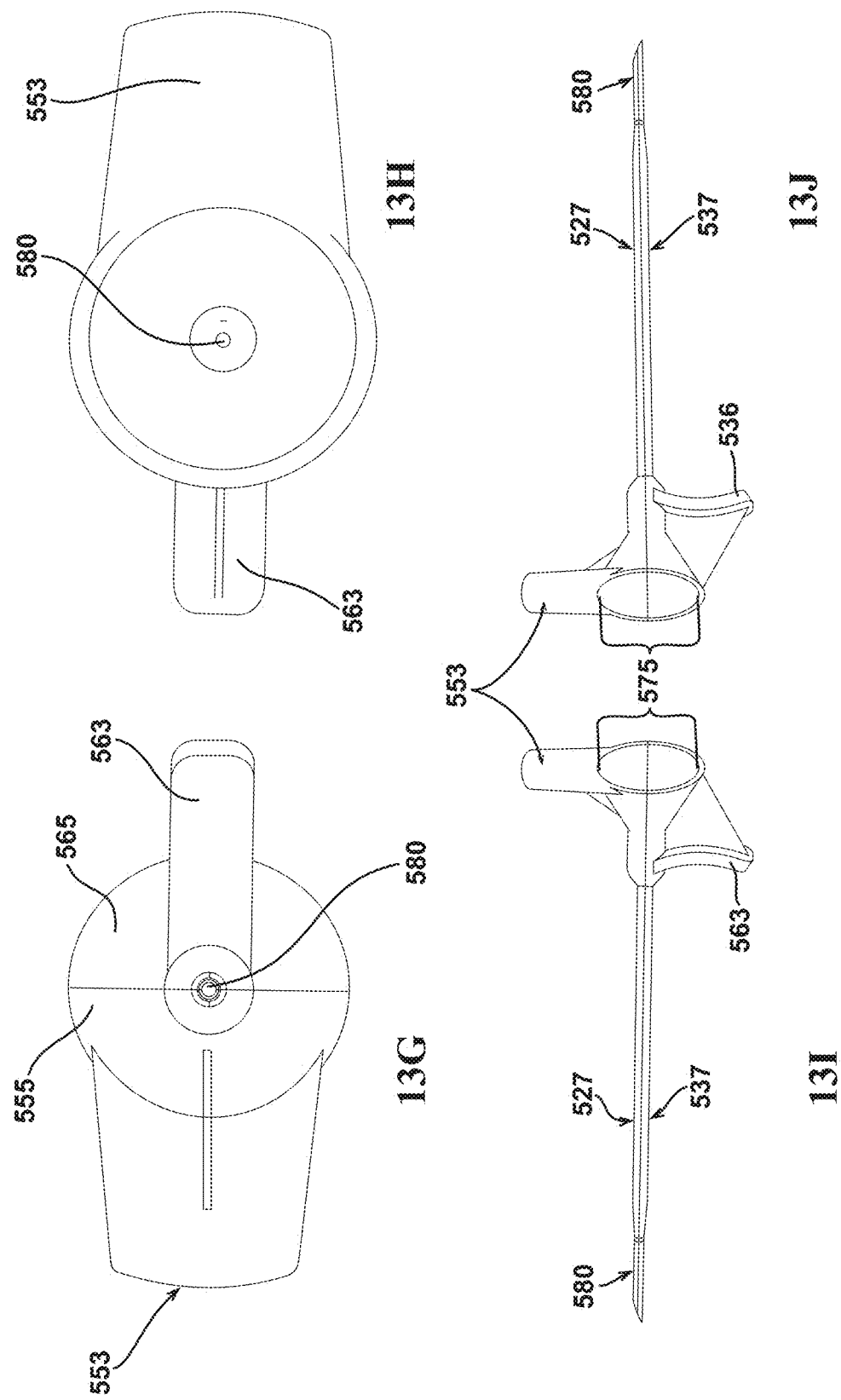
FIGS. 13G-13J show additional perspective views of the first user-assisted sliding hinged disassembling needle of FIGS. 13A and 13B, shown in its assembled state.
Figures 13K, 13L, 13M, 13N:
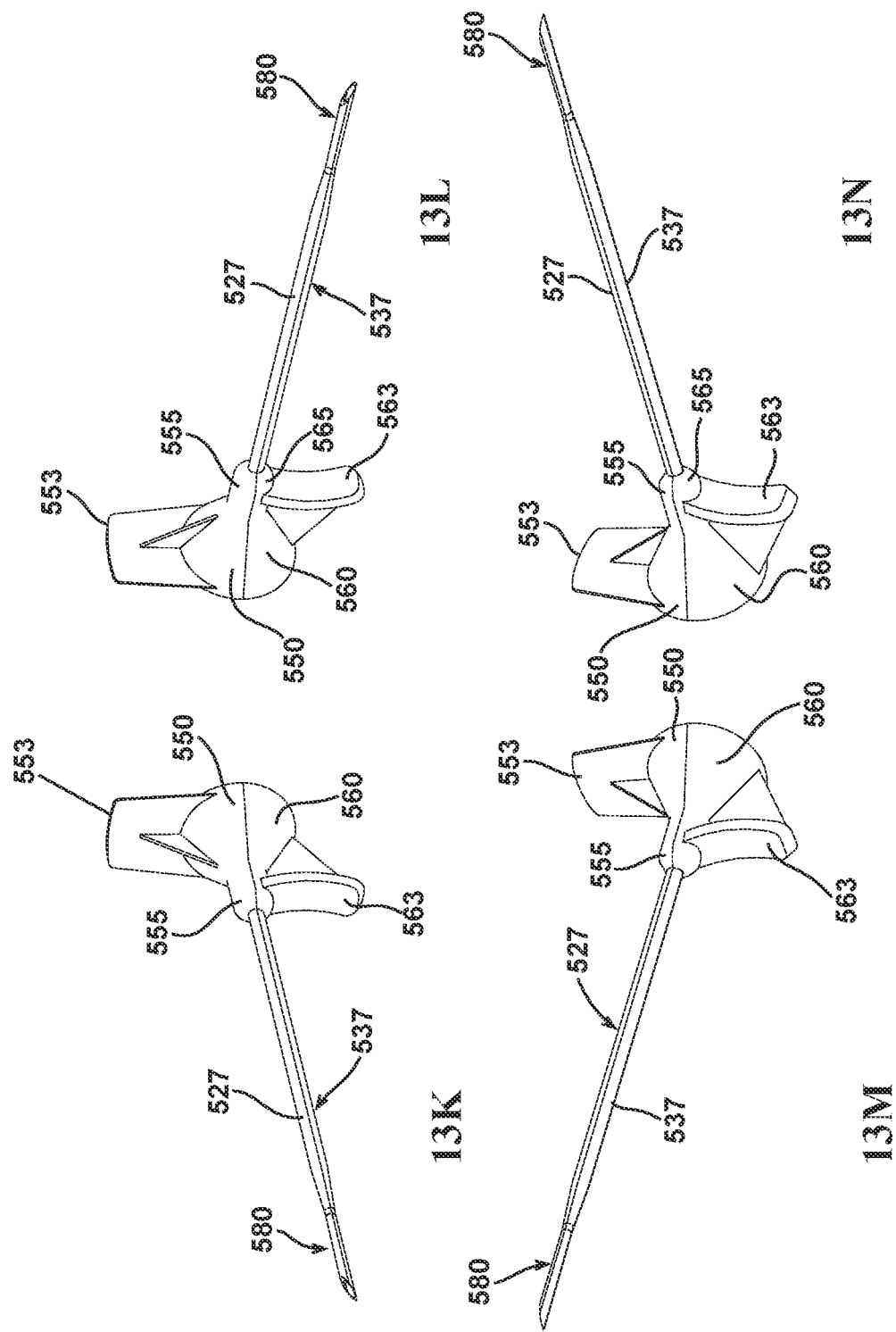
FIGS. 13K-13N show additional perspective views of the first user-assisted sliding hinged disassembling needle of FIGS. 13A and 13B, shown in its assembled state.

FIGS. 13A-13N show various plane and perspective views of a first user-assisted sliding disassembling needle 500, where FIGS. 13A and 13B show the components of this embodiment in two complementary exploded states. More specifically, the first user-assisted disassembling needle 500 includes two engaging actuator halves 550, 560, and a longitudinal cylindrical needle shaft 580, which is formed by two needle shaft halves 520, 530, each of which having its own overlapping sleeve 527, 537, respectively. The overlapping sleeves 527, 537 act similarly to a retaining ring, keeping the two needle shaft halves 520, 530 together. A first actuator half 550 includes a distal motion tab 553 and a collar segment 555, and a second actuator half 560 includes a proximal motion tab 563 and a collar segment 565. Each of the first and second actuator halves 550, 560 are connected to its respective needle shaft half 520, 530 by collar segment 555, 565 that mate with or affixes to proximal end 522, 532. The distal ends 523, 533 of the overlapping sleeves 527, 537 may have a frustoconical shape to enable a gradual expansion in circumference from the longitudinal cylindrical needle shaft 580 to an outer surface of the overlapping sleeves. The first and second actuator halves 550, 560 are similarly connected to its respective overlapping sleeve 527, 537 by collar segment 555, 565 that mate with or affixes to proximal end 529, 539. The assembly of the two interlocking halves 550, 560 creates a conical receiver 575 that accepts a syringe and a longitudinal cylindrical needle 580 that accepts a guidewire. The distal motion and proximal motion tabs (553, 563) may include ridges or other raised or roughened features to enhance the surgeons grasp on the tabs (553, 563) of the disassembling needle 500 when splitting the longitudinal cylindrical needle 580. The tabs (553, 563) may also be coated in material, such as rubber, to enhance the surgeon's grasp while splitting the disassembling needle 500.

The distal motion and proximal motion tabs (553, 563) are connected to their corresponding needle shaft half 520, 530, and overlapping sleeves 527, 537, which may be configured to slidably engage. In an embodiment, the overlapping sleeves 527, 537 are slotted with tongue-in-groove rails comprising tabs 526 and slots 536 that lock in a neutral position, but unlock as the first and second actuator halves 550, 560 are advanced in the opposing longitudinal direction. Accordingly, applying opposing forces to the distal motion and proximal motion tabs 553, 563 causes relative longitudinal motion in opposite directions and will allow the two parts of the slotted sleeves 527, 537 to disassemble, thereby also permitting the two halves of the needle shaft 520, 530 to separate. This enables the interlocking halves to slide off of each other and allows for separation of the contralateral seams 370 (FIG. 13C) and 372 (FIG. 13D) in the shaft 580 of the needle 500. In an embodiment, the distal motion and proximal motion tabs 553, 563 are maintained in the neutral position by a removable (or unlockable) interlocking member (not shown), such as a tab, pin, or latch. FIGS. 13C and 13D show the assembled state of the disassembling needle 500 from opposing side views, while FIGS. 13E and 13F show the assembled state of the disassembling needle 500 from opposing top and bottom views, respectively. FIGS. 13G and 13H show the assembled state of the disassembling needle 500 from a front view and a back view, respectively. FIG. 13I through FIG. 13N show complementary assembled state perspective views of the disassembling needle 500.

Figures 14A, 14B:
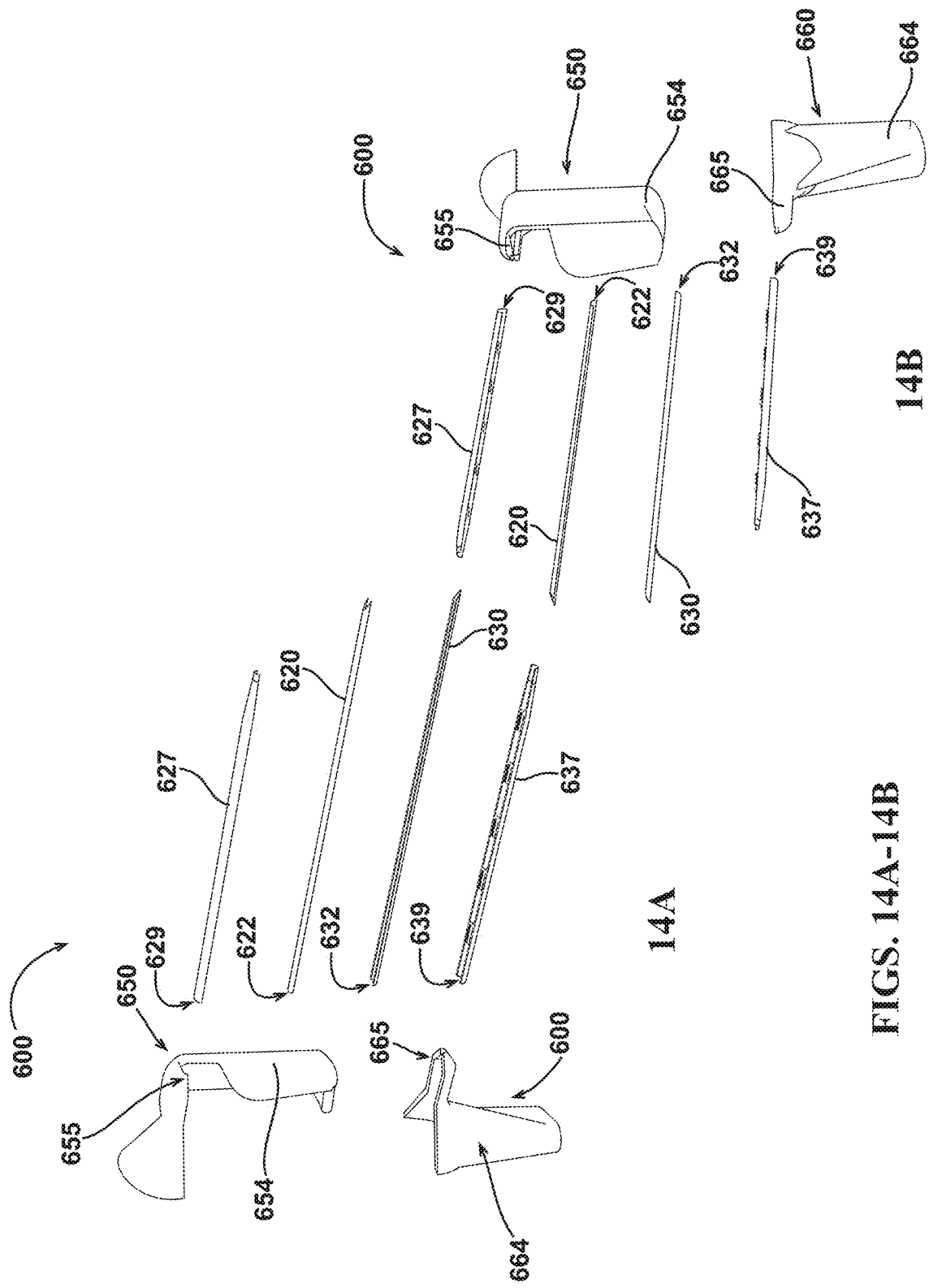
FIGS. 14A and 14B show two complementary perspective views of a second user-assisted sliding disassembling needle embodiment, where the components of this embodiment are shown in exploded states.

FIGS. 14A-14N show various plane and perspective views of a second user-assisted sliding disassembling needle 600, where FIGS. 14A and 14B show the components of this embodiment in two complementary exploded states. More specifically, the second user-assisted disassembling needle 600 includes two engaging actuator halves 650, 660, and a longitudinal cylindrical needle shaft 680, which is formed by two needle shaft halves 620, 630, each of which having its own overlapping sleeve 627, 637, respectively. The overlapping sleeves 627, 637 act similarly to a retaining ring, keeping the two needle shaft halves 620, 630 together. A first actuator half 650 includes a first handle portion 654 and a collar segment 655, and a second actuator half 660 includes a second handle portion 664 and a collar segment 665. Each of the first and second actuator halves 650, 660 are connected to its respective needle shaft half 620, 630 by collar segment 655, 665 that mate with or affixes to proximal end 622, 632. The first and second actuator halves 650, 660 are similarly connected to its respective overlapping sleeve 627, 637 by collar segment 655, 665 that mate with or affixes to proximal end 629, 639. The distal ends 623, 633 of the overlapping sleeves 627, 637 may have a frustoconical shape to enable a gradual expansion in circumference from the longitudinal cylindrical needle shaft 680 to an outer surface of the overlapping sleeves. The assembly of the two engaging actuator halves 650, 660 creates a conical receiver 675 that accepts a syringe and a longitudinal cylindrical needle 680 that accepts a guidewire. The first and second handle portions (654, 664) may include ridges or other raised or roughened features to enhance the surgeons grasp when a squeezing motion is caused to split the longitudinal cylindrical needle 680. The first and second handle portions (654, 664) may also be coated in material, such as rubber, to enhance the surgeon's grasp while splitting the disassembling needle 600.

The first and second handle portions (654, 664) are connected to their corresponding needle shaft half 620, 630, and overlapping sleeves 627, 637, which may be configured to slidably engage. Similar to that described above, the overlapping sleeves 627, 637 may be slotted with tongue-in-groove rails that are locked in a neutral position, but unlock as the first and second handle portions 654, 664 are squeezed together. This squeezing force causes relative longitudinal motion in opposite directions and allows the two halves of the needle shaft 620, 630 and slotted sleeve 627, 637 to disassemble, thereby also permitting the two halves of the needle shaft 620, 630 to separate. This enables the interlocking halves to slide off of each other and allows for separation of the contralateral seams 670 (FIG. 14C) and 672 (FIG. 14D) in the shaft 680 of the needle 600. FIGS. 14C and 14D show the assembled state of the disassembling needle 600 from opposing side views, while FIGS. 14E and 14F show the assembled state of the disassembling needle 600 from opposing top and bottom views, respectively. FIGS. 14G and 14H show the assembled state of the disassembling needle 600 from a front view and a back view, respectively. FIG. 14I through FIG. 14N show complementary assembled state perspective views of the disassembling needle 600.

Figures 15A, 15B:
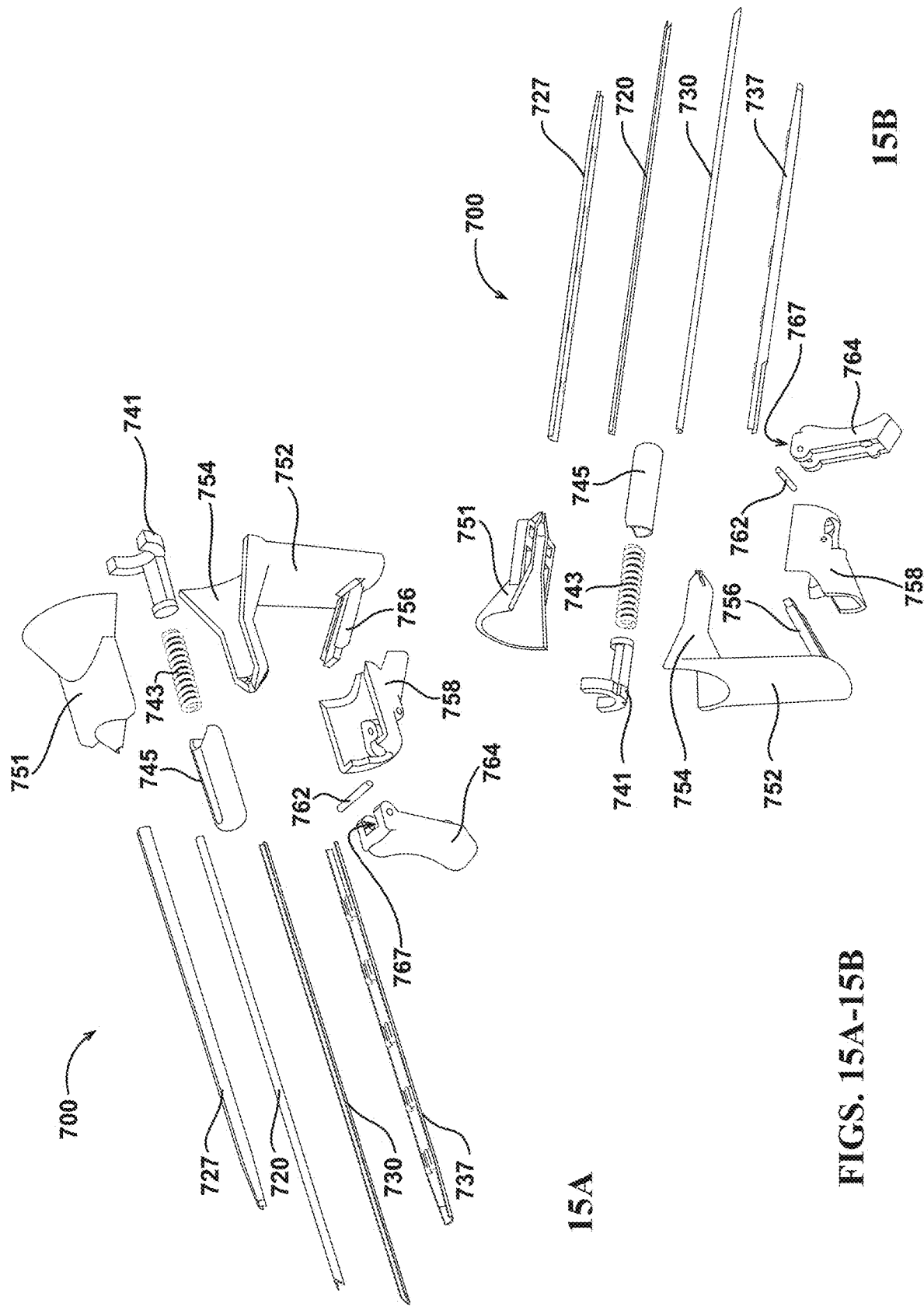
FIGS. 15A and 15B show various perspective views of a mechanically-assisted sliding disassembling needle, where the components of this embodiment are shown in exploded states.
Figures 15C, 15D, 15E, 15F:
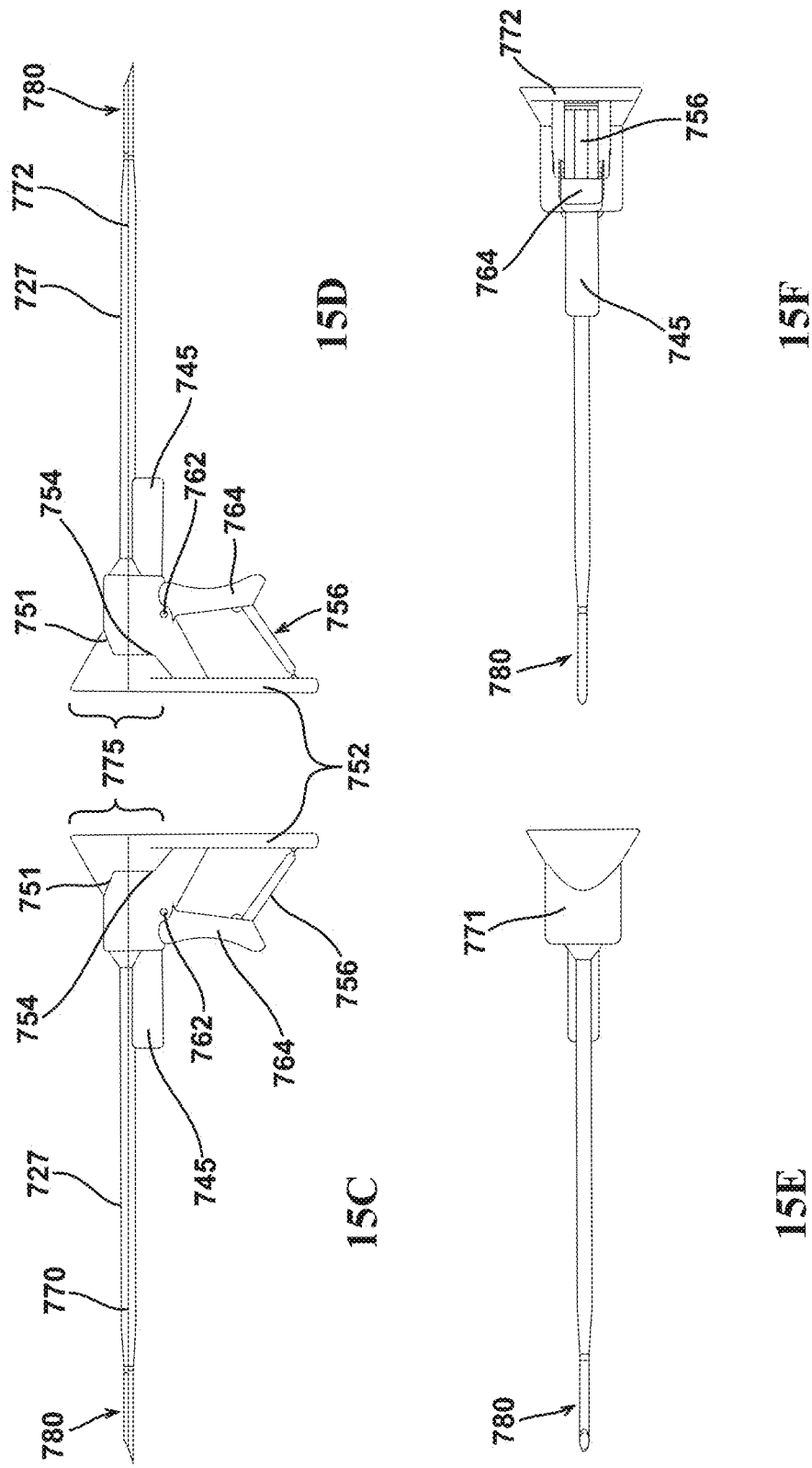
FIGS. 15C-15F show additional perspective views of the mechanically-assisted sliding hinged disassembling needle of FIGS. 15A and 15B, shown in its assembled state.
Figures 15G, 15H, 15I, 15J:
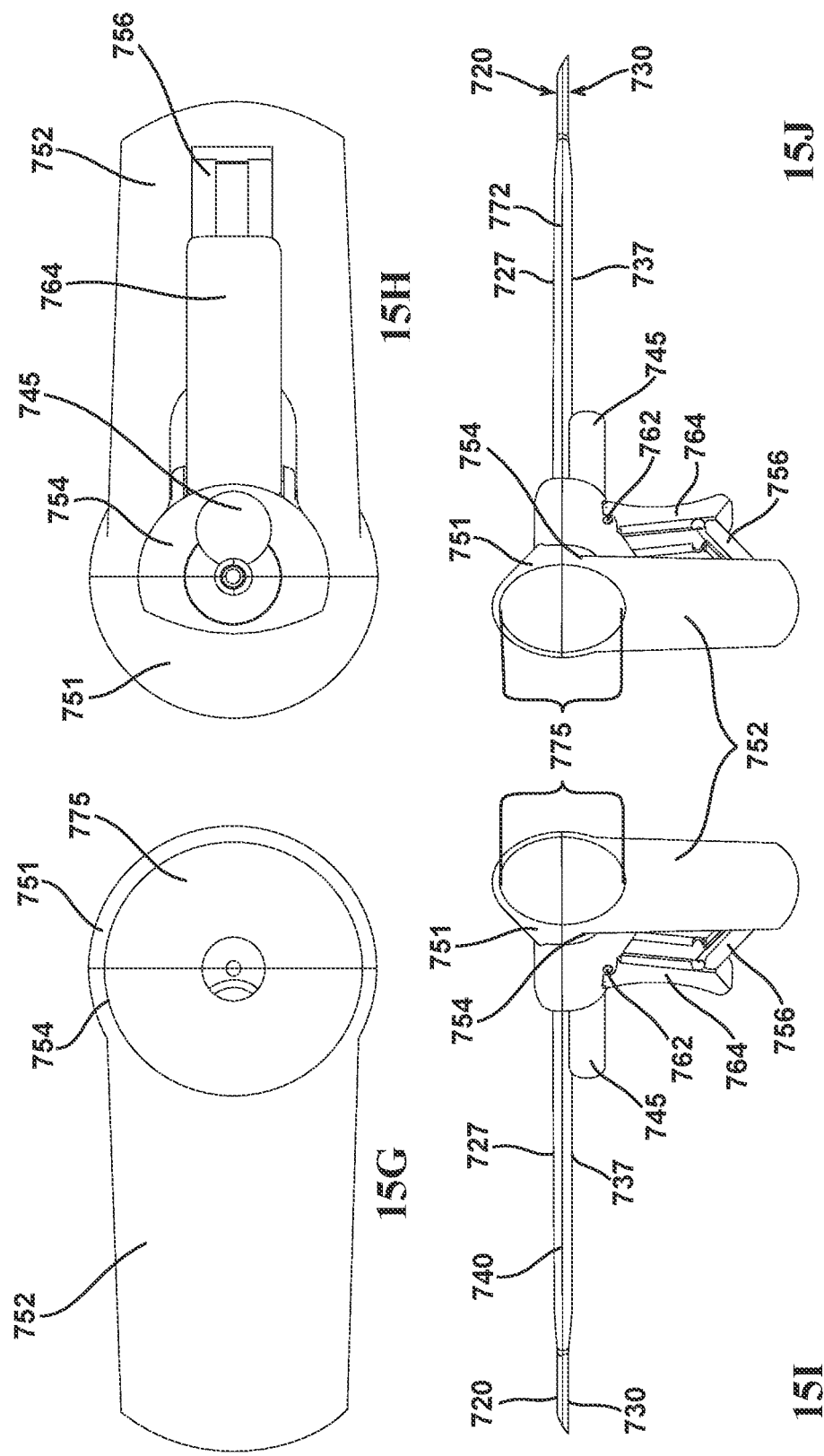
FIGS. 15G-15J show additional perspective views of the mechanically-assisted sliding hinged disassembling needle of FIGS. 15A and 15B, shown in its assembled state.
Figures 15K, 15L, 15M, 15N:
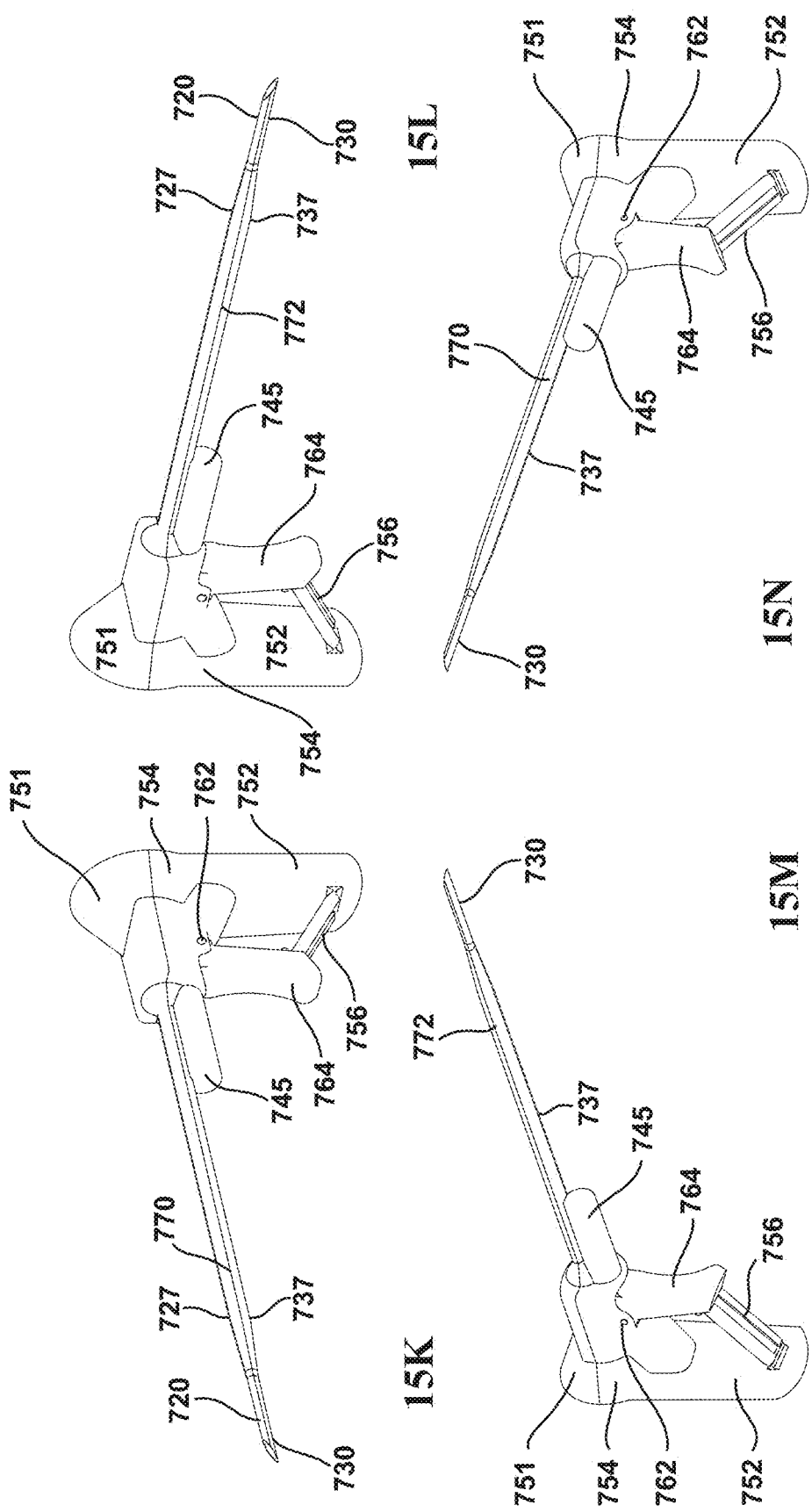
FIGS. 15K-15N show additional perspective views of the mechanically-assisted sliding hinged disassembling needle of FIGS. 15A and 15B, shown in its assembled state.

FIGS. 15A-15N show various plain and perspective views of a mechanically-assisted sliding disassembling needle 700. Similar to disassembling needles 500 and 600, this embodiment also includes a longitudinal cylindrical needle shaft 780, which is formed by two needle shaft halves 720, 730, each of which having its own overlapping sleeve 727, 737, respectively. The needle shaft halves 720, 730 and overlapping sleeves 727, 737 are configured to slidably engage. Similar to that described above, the overlapping sleeves 727, 737 may be slotted with tongue-in-groove rails that are locked in a neutral position, but unlock as an opposing longitudinal force causes relative longitudinal motion of the opposing halves in opposite directions and allows the two halves of the needle shaft 720, 730 and slotted sleeve 727, 737 to disassemble. The separation of the contralateral seams 770 (FIG. 15C) and 772 (FIG. 15D) in the needle shaft halves 720, 730 and overlapping sleeves 727, 737 enables the interlocking halves to slide off of each other to free the guidewire.

The mechanically-assisted sliding disassembling needle 700 further includes a spring assembly 710, which facilitates the sliding action of a superior needle shaft half 720 and superior overlapping sleeve 727 in relation to an inferior needle shaft half 730 and inferior overlapping sleeve 737 to allow the two halves of the needle shafts and overlapping sleeves to become unbound from each other and disassemble. In an embodiment, the superior needle shaft half 720 and superior the overlapping sleeve 727 are each fixed or attached to an upper conical receiver 751, and may be collectively be referred to as a "movable upper half."

A corresponding "stationary lower half" includes the inferior needle shaft half 730, the inferior overlapping sleeve 737, the piston 741, the spring 743, the spring housing 745, a safety tab 756, a piston shroud 758, a trigger 764, a hinge pin 762, a lower conical receiver 754, which also includes a handle 752 extending therefrom. For purposes of this description, the lower stationary half components may be considered to be operatively attached to each other, and considered to be stationary, relative to the movable upper half. The handle 752 and the lower conical receiver 754 may be constructed as a single body. Attached to the lower conical receiver 754, there is the cylindrical spring housing 745 which contains a compressed steel helical spring 743. Also attached to the lower stationary half is a piston shroud 758 which contains a movable piston 741, which holds the spring 743 in the compressed state. The piston 741 has tabs which slot into recesses on the upper conical receiver 751. The piston shroud 758 also provides a mounting point for the trigger 764 which is held in place by the hinge pin 762. The trigger 764 may contain a detent 767 on the top that holds the piston 762 in neutral position, thereby keeping the spring 743 compressed. There is also a safety tab 756 attached to the distal end of the handle 752 of the lower conical receiver 754 that interfaces with the trigger 764, keeping it in the neutral position until sufficient force is applied to overcome and release the safety tab 756, initiating the motion sequence.

Once a sufficient force is applied to the trigger 764, the safety tab 756 releases to allow the trigger 764 to pivot backward causing the trigger detent 767 to drop thereby releasing the piston 762. The spring 743 pushes the movable piston 741 backward, which consequently moves the movable upper half backward causing the interlocking features on the upper and lower sleeves 727, 737 to disengage and allowing the movable upper half to completely separate from the stationary lower half.

FIGS. 15C and 15D show the assembled state of the disassembling needle 700 from opposing side views, while FIGS. 15E and 15F show the assembled state of the disassembling needle 700 from opposing top and bottom views, respectively. FIGS. 15G and 15H show the assembled state of the disassembling needle 700 from a front view and a back view, respectively. FIG. 15I through FIG. 15N show complementary assembled state perspective views of the disassembling needle 700.

Thus configured, the various embodiments of the disassembling needle reduces the number of steps required to insert a device percutaneously. The method of the present invention simplifies the steps in the Seldinger technique and permits pre-loading of the catheter on the guidewire by eliminating the need to slide the needle along the length of the guidewire for its removal. In accordance with an embodiment of the present invention, the disassembling needle does not require the use of a separate introducer sheath. Consequently, the size of the assembly is reduced and wear and tear on a subject's blood vessel can be minimized. The disassembling needle delivers an all-in-one device intended to minimize manipulation of a guide wire for delivery of various medical devices within a subject's vasculature.

Various embodiments of the present invention have been particularly shown and described with respect to certain preferred embodiments and features thereof. However, it should be readily apparent to those of ordinary skill in the art that various changes and modifications in form and detail may be made without departing from the spirit and scope of the inventions as set forth herein and the appended claims.

We claim:

1. A vascular access disassembling needle, comprising:
   a pair of semicylindrical needle tube portions configured to be joined together;
   a separation seam extending from the distal end to the proximal end, wherein the separation seam is formed when the pair of semicyclindrical needle tube portions are joined; and
   a bendable seam extending from the distal end to the proximal end of the disassembling needle, the opposing bendable seam opposing the separation seam when the pair of semicyclindrical needle tubes portions are joined;
   an extension member extending proximally from the proximal end of each of the pair of semicyclindrical needle tube portions;
   first and second interlocking halves operably coupled to proximal ends of respective ones of the pair of semicyclindrical needle tube portions and configured to form a conical collar when the pair of semicyclindrical needle tube portions are joined, each of the first and second interlocking halves having a wing extending radially outwardly from the respective first or second interlocking half,
   wherein the wings are substantially perpendicular with respect to each other when the pair of semicyclindrical needle tube portions are joined and are configured such that when a squeezing force is applied to the wings the pair of semicyclindrical needle tube portions split at the separation seam and the pair of semicyclindrical needle tube portions pivot at the bendable seam.

2. The vascular access disassembling needle of claim 1 wherein the extension members are configured to form a female docking portion when the pair of semicyclindrical needle tube portions are joined, the female docking portion configured to receive a male docking portion of a syringe.

3. The vascular access disassembling needle of claim 1, wherein
   the conical collar is configured to receive a male docking portion of a syringe and wherein the wings join at an offset hinge portion that is radially disposed exterior to the needle tube.

4. The vascular access disassembling needle of claim 1, wherein each of the
   first and second interlocking halves includes longitudinally-extending tab extending therefrom and configured to form a pivot region that serves as a fulcrum.

* * * * *